United States Patent [19]

Boller et al.

[11] 4,273,929

[45] Jun. 16, 1981

[54] HETEROCYCLIC COMPOUNDS

[75] Inventors: Arthur Boller, Binningen; Martin Schadt, Seltisberg; Alois Villiger, Basel, all of Switzerland

[73] Assignee: Hoffmann-La Roche Inc., Nutley, N.J.

[21] Appl. No.: 116,518

[22] Filed: Jan. 29, 1980

[30] Foreign Application Priority Data

Feb. 5, 1979 [CH] Switzerland .......................... 1102/79
Jun. 27, 1979 [CH] Switzerland .......................... 5996/79
Nov. 13, 1979 [CH] Switzerland .......................... 10126/79

[51] Int. Cl.$^3$ .................... C09K 3/34; G02F 1/13; C07D 239/26
[52] U.S. Cl. .................................. 544/242; 252/408; 350/350 R; 544/335; 252/299.61
[58] Field of Search .................. 252/299, 408; 350/350 R; 544/242, 335

[56] References Cited

U.S. PATENT DOCUMENTS

| | | | |
|---|---|---|---|
| 3,997,536 | 12/1976 | Boller et al. | 252/299 |
| 4,062,798 | 12/1977 | Boller et al. | 252/299 |
| 4,130,502 | 12/1978 | Eidenschink et al. | 252/299 |
| 4,145,114 | 3/1979 | Coates et al. | 252/299 |
| 4,154,697 | 5/1979 | Eidenschink et al. | 252/299 |
| 4,180,475 | 12/1979 | Schadt et al. | 252/299 |
| 4,181,625 | 1/1980 | Eidenschink et al. | 252/299 |
| 4,198,130 | 4/1980 | Boller et al. | 252/299 |

FOREIGN PATENT DOCUMENTS

| | | | |
|---|---|---|---|
| 137242 | 8/1979 | German Democratic Rep. | 252/299 |
| 139852 | 1/1980 | German Democratic Rep. | 252/299 |
| 139867 | 1/1980 | German Democratic Rep. | 252/299 |
| 2257588 | 6/1973 | Fed. Rep. of Germany | 252/299 |
| 2815860 | 10/1978 | Fed. Rep. of Germany | 252/299 |
| 2841245 | 7/1979 | Fed. Rep. of Germany | 252/299 |

OTHER PUBLICATIONS

Cox, R. J., Mol. Cryst. Liq. Cryst., vol. 55, pp. 1–32 (1979).
Constant, J., et al., "Photostable Anthraquinone Pleochroic Dyes", presented at 7th Int. L.C. Conf., Bordeaux, France (Aug. 1978).
Demus, D., et al., Mol. Cryst. Liq. Cryst., vol. 15, pp. 161–174 (1971).
Gray, G. W., et al., Mol. Cryst. Liq. Cryst., vol. 53, pp. 147–166 (1979).

*Primary Examiner*—Teddy S. Gron
*Attorney, Agent, or Firm*—Jon S. Saxe; Bernard S. Leon; William G. Isgro

[57] ABSTRACT

Pyrimidine derivatives of the formula

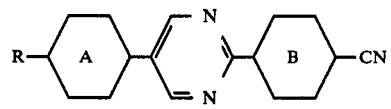

wherein at least one of rings A and B is a trans-1,4-disubstituted cyclohexane ring and the other, optionally, may be aromatic and R is straight-chain alkyl or alkoxy of 1 to 10 carbon atoms or a branched-chain alkyl group of the formulas $C_2H_5$—$CH(CH_3)$—$(CH_2)_n$—wherein n is 1, 2 or 3, are described. Processes for the preparation of the compounds of formula I as well as their uses in liquid crystalline mixtures are also described.

7 Claims, No Drawings

HETEROCYCLIC COMPOUNDS

BRIEF SUMMARY OF THE INVENTION

The invention relates to pyrimidine derivatives of the formula

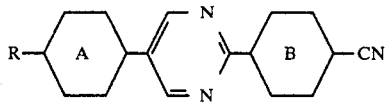

wherein at least one of the rings A and B is a trans-1,4-disubstituted cyclohexane ring and the other is optionally aromatic and R is straight-chain alkyl or alkoxy containing 1 to 10 carbon atoms or a branched-chain alkyl group of the formula C$_2$H$_5$—CH(CH$_3$)—(CH$_2$)$_n$—wherein n is 1, 2 or 3.

In another aspect, the invention relates to a process for the preparation of the pyrimidine derivatives of formula I which comprises dehydrating a compound of the formula

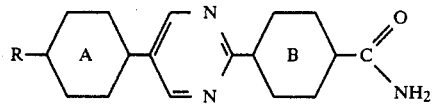

wherein A, B and R are as previously described, or, for the preparation of pyrimidine derivatives of formula I wherein ring A is a cyclohexyl ring and ring B is a benzene ring, by reacting a compound of the formula

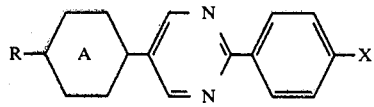

wherein R and A are as previously described and X is fluorine, chlorine or bromine, with copper-(I) cyanide, sodium cyanide or potassium cyanide.

In yet another aspect, the invention relates to nematic and cholesteric mixtures which contain the pyrimidine derivatives of formula I and, if desired, dichroic coloring substances; electro-optical apparatuses which contain pyrimidine derivatives of formula I; the use of pyrimidine derivatives of formula I for electro-optical purposes; and the manufacture of said mixtures and apparatuses.

The pyrimidine derivatives of formula I are particularly valuable as components of liquid crystalline mixtures and, for the most part, they themselves possess liquid crystalline properties. The compounds of formula I exhibit an especially large mesophase range with high clearing points, a large positive anisotropy of the dielectric constants and, as a result, have a low threshold potential, a short relay time and high chemical stability.

DETAILED DESCRIPTION OF THE INVENTION

The invention relates to pyrimidine derivatives of the formula

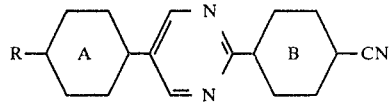

wherein at least one of rings A and B is a trans-1,4-disubstituted cyclohexane ring and the other is optionally an aromatic ring and R is straight-chain alkyl or alkoxy containing 1 to 10 carbon atoms or a branched-chain alkyl group of the formula C$_2$H$_5$—CH(CH$_3$)—(CH$_2$)$_n$—wherein n is 1, 2 or 3.

The invention also relates to a process for the preparation of the pyrimidine derivatives of formula I hereinbefore, nematic and cholesteric mixtures containing said pyrimidine derivatives and the use of said derivatives in electro-optical apparatuses.

The pyrimidine derivatives of formula I are particularly valuable as components of liquid crystalline mixtures and, for the most part, the compounds of formula I themselves possess liquid crystalline properties. The pyrimidine derivatives of formula I, which contain a straight side-chain, form a nematic meso phase, while the optically active pyrimidine derivatives of formula I which contain a branched side-chain form a cholesteric meso phase. The pyrimidine derivatives of formula I possess, inter alia, a very high positive anisotropy of the dielectric constants ($\epsilon_{\parallel} > \epsilon_{\perp}$, $\epsilon_{\parallel}$ signifies the dielectric constant along the longitudinal axis of the molecule and $\epsilon_{\perp}$ signifies the dielectric constant perpendicular thereto).

In an electric field, the pyrimidine derivatives of formula I orientate themselves (because $\epsilon_{\parallel} > \epsilon_{\perp}$) with the direction of their largest dielectric constant, that is, with their longitudinal axes, parallel to the field direction. This effect is used, inter alia, in the interaction between embedded molecules and the liquid crystalline molecules (guest-host interaction) described by J. H. Heilmeier and L. A. Zanoni [Applied Physics Letters 13, 91 (1968)]. A further interesting application of the dielectric field orientation exists in the rotation cell discovered by M. Schadt and W. Helfrich [Applied Physics Letters 18, (1971)] and in the Kerr cell described in Molecular Crystals and Liquid Crystals 17, 355 (1972).

The electro-optical rotation cell is essentially a condenser having transparent electrodes, the dielectric of which is formed from a nematic crystal with $\epsilon_{\parallel} > \epsilon_{\perp}$. The longitudinal molecular axes of the liquid crystals are arranged in twisted form between the condenser plates in the fieldless state, the twisting structure being determined by the given wall orientation of the molecules. Upon the application of an electric potential to the condenser plates, the molecules adjust themselves with their longitudinal axes in the field direction, that is, perpendicular to the surface of the plates, by which means linear polarized light is no longer rotated in the dielectric (the liquid crystal is uniaxially perpendicular to the surface of the plates). This effect is reversible and can be used to electrically control the optical transmissivity of the condenser.

In such a "light rotation cell" it is, inter alia, desirable to use compounds or mixtures which possess a low threshold potential, this is important, for example, when a rotation cell is used in pocket calculators, and the like.

Further, it is known that the addition of cholesteric substances to a matrix of nematic liquid crystals with positive anisotropy of the dielectric constants leads to a cholesteric mixture which undergoes a cholesteric-nematic phase transition by the application of an electric field. This phase transition is reversible and makes possible high switching times of electro-optical apparatuses which operate with such mixtures.

It has now been found in accordance with the invention that the pyrimidine derivatives of formula I have a particularly large mesophase range with high clearing points and that, therefore, they are particularly suitable for increasing the clearing points of nematic mixtures. In addition, the pyrimidine derivatives of formula I not only possess the required large positive anisotropy of the dielectric constants, and consequently, low threshold potentials, in indicator devices based on a field effect, for example, the rotation cell described earlier, but they exhibit a short relay time and a high chemical stability. Furthermore, the pyrimidine derivatives of formula I considerably reduce, in indicator devices based on a field effect, the temperature dependence of the optical transmission curves when they are mixed with other liquid crystalline substances such as, for example, para-cyano-substituted Schiffs bases, esters or biphenyls. This property renders the pyrimidine derivatives of formula I particularly valuable for multiplex working in indicator devices having a low threshold potential. A further advantage of the pyrimidine derivatives of formula I is that they are colorless. Mixtures which contain the pyrimidine derivatives of formula I are characterized by a ready orientability and slight smectic tendencies, and provide a high contrast in indicator devices.

The pyrimidine derivatives falling within formula I hereinbefore are either trans-p-[5-(4-alkyl- or 4-n-alkoxy-cyclohexyl)-2-pyrimidinyl]benzonitriles of the formula

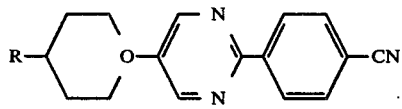

IA

, trans-4-[5-(p-alkyl- or p-n-alkoxyphenyl)-2-pyrimidinyl]-cyclohexane carbonitriles of the formula

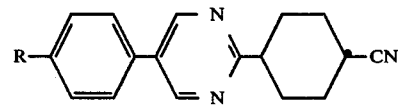

IB or trans-4-[5-(trans-4-alkyl- or trans-4-n-alkoxycyclohexyl)-2-pyrimidinyl]cyclohexane carbonitriles of the formula

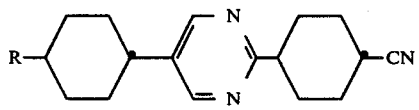

IC wherein R is as previously described.

Of the pyrimidine derivatives of formulas IA, IB and IC, those of formula IA are preferred, and particularly, those of formula IA wherein R is alkyl. When R is alkyl, preferred, in the compounds of formulas IA, IB and IC, are those wherein the alkyl group is 2 to 8 carbon atoms, especially 2 to 7 carbon atoms. When R is alkoxy, preferred are alkoxy groups containing up to 6 carbon atoms.

Examples of pyrimidine derivatives of formula I hereinbefore are:
Trans-p-[5-(4-methylcyclohexyl)-2-pyrimidinyl]benzonitrile;
trans-p-[5-(4-ethylcyclohexyl)-2-pyrimidinyl]benzonitrile;
trans-p-[5-(4-propylcyclohexyl)-2-pyrimidinyl]benzonitrile;
trans-p-[5-(4-butylcyclohexyl)-2-pyrimidinyl]benzonitrile; trans-p-[5-(4-pentylcyclohexyl)-2-pyrimidinyl]benzonitrile;
trans-p-[5-(4-hexylcyclohexyl)-2-pyrimidinyl]benzonitrile;
trans-p-[5-(4-heptylcyclohexyl)-2-pyrimidinyl]benzonitrile; trans-p-[5-(4-octylcyclohexyl)-2-pyrimidinyl]benzonitrile;
trans-p-[5-(4-nonylcyclohexyl)-2-pyrimidinyl]benzonitrile;
trans-p-[5-(4-decylcyclohexyl)-2-pyrimidinyl]benzonitrile; trans-p-[5-(4-methoxycyclohexyl)-2-pyrimidinyl]benzonitrile;
trans-p-[5-(4-ethoxycyclohexyl)-2-pyrimidinyl]benzonitrile;
trans-p-[5-(4-propyloxycyclohexyl)-2-pyrimidinyl]benzonitrile;
trans-p-[5-(4-butyloxycyclohexyl)-2-pyrimidinyl]benzonitrile;
trans-p-[5-(4-pentyloxycyclohexyl)-2-pyrimidinyl]benzonitrile;
trans-p-[5-(4-hexyloxycyclohexyl)-2-pyrimidinyl]benzonitrile;
trans-p-[5-(4-heptyloxycyclohexyl)-2-pyrimidinyl]benzonitrile;
trans-p-[5-(4-octyloxycyclohexyl)-2-pyrimidinyl]benzonitrile;
trans-p-[5-(4-nonyloxycyclohexyl)-2-pyrimidinyl]benzonitrile;
trans-p-[5-(4-decyloxycyclohexyl)-2-pyrimidinyl]benzonitrile;
trans-4-[5-(p-methylphenyl)-2-pyrimidinyl]cyclohexane carbonitrile;
trans-4-[5-(p-ethylphenyl)-2-pyrimidinyl]cyclohexane carbonitrile;
trans-4-[5-(p-propylphenyl)-2-pyrimidinyl]cyclohexane carbonitrile;
trans-4-[5-(p-butylphenyl)-2-pyrimidinyl]cyclohexane carbonitrile;
trans-4-[5-(p-pentylphenyl)-2-pyrimidinyl]cyclohexane carbonitrile;
trans-4-[5-(p-hexylphenyl)-2-pyrimidinyl]cyclohexane carbonitrile;
trans-4-[5-(p-heptylphenyl)-2-pyrimidinyl]cyclohexane carbonitrile;
trans-4-[5-(p-octylphenyl)-2-pyrimidinyl]cyclohexane carbonitrile;
trans-4-[5-(p-nonylphenyl)-2-pyrimidinyl]cyclohexane carbonitrile;
trans-4-[5-(p-decylphenyl)-2-pyrimidinyl]cyclohexane carbonitrile;
trans-4-[5-(p-methoxyphenyl)-2-pyrimidinyl]cyclohexane carbonitrile;
trans-4-[5-(p-ethoxyphenyl)-2-pyrimidinyl]cyclohexane carbonitrile;
trans-4-[5-(p-propyloxyphenyl)-2-pyrimidinyl]cyclohexane carbonitrile;

trans-4-[5-(p-butyloxyphenyl)-2-pyrimidinyl]cyclohexane carbonitrile;
trans-4-[5-(p-pentyloxyphenyl)-2-pyrimidinyl]cyclohexane carbonitrile;
trans-4-[5-(p-hexyloxyphenyl)-2-pyrimidinyl]cyclohexane carbonitrile;
trans-4-[5-(p-heptyloxyphenyl)-2-pyrimidinyl]cyclohexane carbonitrile;
trans-4-[5-(p-octyloxyphenyl)-2-pyrimidinyl]cyclohexane carbonitrile;
trans-4-[5-(p-nonyloxyphenyl)-2-pyrimidinyl]cyclohexane carbonitrile;
trans-4-[5-(p-decyloxyphenyl)-2-pyrimidinyl]cyclohexane carbonitrile;
trans-4-[5-(trans-4-methylcyclohexyl)-2-pyrimidinyl]cyclohexane carbonitrile;
trans-4-[5-(trans-4-ethylcyclohexyl)-2-pyrimidinyl]cyclohexane carbonitrile;
trans-4-[5-(trans-4-propylcyclohexyl)-2-pyrimidinyl]cyclohexane carbonitrile;
trans-4-[5-(trans-4-butylcyclohexyl)-2-pyrimidinyl]cyclohexane carbonitrile;
trans-4-[5-(trans-4-pentylcyclohexyl)-2-pyrimidinyl]cyclohexane carbonitrile;
trans-4-[5-(trans-4-hexylcyclohexyl)-2-pyrimidinyl]cyclohexane carbonitrile;
trans-4-[5-(trans-4-heptylcyclohexyl)-2-pyrimidinyl]cyclohexane carbonitrile;
trans-4-[5-(trans-4-octylcyclohexyl)-2-pyrimidinyl]cyclohexane carbonitrile;
trans-4-[5-(trans-4-nonylcyclohexyl)-2-pyrimidinyl]cyclohexane carbonitrile;
trans-4-[5-(trans-4-decylcyclohexyl)-2-pyrimidinyl]cyclohexane carbonitrile;
trans-4-[5-(trans-4-methoxycyclohexyl)-2-pyrimidinyl]cyclohexane carbonitrile;
trans-4-[5-(trans-4-ethoxycyclohexyl)-2-pyrimidinyl]cyclohexane carbonitrile;
trans-4-[5-(trans-4-propyloxycyclohexyl)-2-pyrimidinyl]cyclohexane carbonitrile;
trans-4-[5-(trans-4-butyloxycyclohexyl)-2-pyrimidinyl]cyclohexane carbonitrile;
trans-4-[5-(trans-4-pentyloxycyclohexyl)-2-pyrimidinyl]cyclohexane carbonitrile;
trans-4-[5-(trans-4-hexyloxycyclohexyl)-2-pyrimidinyl]cyclohexane carbonitrile;
trans-4-[5-(trans-4-heptyloxycyclohexyl)-2-pyrimidinyl]cyclohexane carbonitrile;
trans-4-[5-(trans-4-octyloxycyclohexyl)-2-pyrimidinyl]cyclohexane carbonitrile;
trans-4-[5-(trans-4-nonyloxycyclohexyl)-2-pyrimidinyl]cyclohexane carbonitrile;
trans-4-[5-(trans-4-decyloxycyclohexyl)-2-pyrimidinyl]cyclohexane carbonitrile;
(+)-trans-p-[5-[4-(2-methylbutyl)cyclohexyl]-2-pyrimidinyl]benzonitrile;
(+)-trans-p-[5-[4-(3-methylpentyl)cyclohexyl]-2-pyrimidinyl]benzonitrile;
(+)-trans-p-[5-[4-(4-methylhexyl)cyclohexyl]-2-pyrimidinyl]benzonitrile;
(+)-trans-4-[5-[p-(2-methylbutyl)phenyl]-2-pyrimidinyl]cyclohexane carbonitrile;
(+)-trans-4-[5-[p-(3-methylpentyl)phenyl]-2-pyrimidinyl]cyclohexane carbonitrile;
(+)-trans-4-[5-[p-(4-methylhexyl)phenyl]-2-pyrimidinyl]cyclohexane carbonitrile;
(+)-trans-4-[5-[trans-4-(2-methylbutyl)cyclohexyl]-2-pyrimidinyl]cyclohexane carbonitrile;
(+)-trans-4-[5-trans-4-(3-methylpentyl)cyclohexyl]-2-pyrimidinyl]cyclohexane carbonitrile; and
(+)-trans-4-[5-[trans-4-(4-methylhexyl)cyclohexyl]-2-pyrimidinyl]cyclohexane carbonitrile;

as well as the antipodes of the optically active derivatives.

Especially preferred pyrimidine derivatives of formula I are:
Trans-p-[5-(4-ethylcyclohexyl)-2-pyrimidinyl]benzonitrile;
Trans-p-[5-(4-pentylcyclohexyl)-2-pyrimidinyl]benzonitrile;
Trans-p-[5-(4-heptylcyclohexyl)-2-pyrimidinyl]benzonitrile.

According to the process of the invention, the pyrimidine derivatives of formula I hereinbefore are prepared by (a) dehydrating a compound of the formula

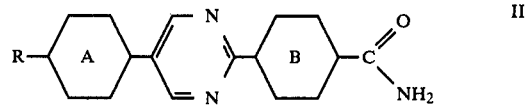

wherein A, B and R are as previously described, or (b) for the preparation of a pyrimidine derivative of formula IA, reacting a compound of the formula

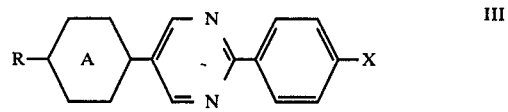

wherein R and A are as previously described and X is fluorine, chlorine or bromine, with copper-(I) cyanide, sodium cyanide or potassium cyanide.

The dehydration of a compound of formula II in accordance with process embodiment (a) can be carried out using any suitable dehydrating agent, for example, phosphorus oxychloride, phosphorus pentoxide, thionyl chloride, acetic anhydride or, especially, benzenesulfonyl chloride and the like. The dehydration can be carried out in an inert organic solvent, for example, a hydrocarbon or halogenated hydrocarbon, and if desired, in the presence of a base such as, sodium acetate, pyridine or triethylamine. However, the dehydration can also be carried out in the absence of an organic solvent. Preferably, the dehydration is carried out at a temperature in the range of 50° C. to the reflux temperature of the mixture. The pressure is not critical; it is, however, advantageous to carry out the dehydration at atmospheric pressure.

The reaction of a compound of formula III with copper-(I) cyanide, sodium cyanide or potassium cyanide in accordance with process embodiment (b) is conveniently carried out in an inert organic solvent, for example, ethyleneglycol, tetrahydrofuran, dimethylformamide, dimethylsulfoxide, pyridine or acetonitrile. The temperature and pressure are not critical aspects of this reaction. The reaction is conveniently carried out at atmospheric pressure and at a temperature in the range of from room temperature to the boiling point of the reaction mixture. In the compound of formula III, X preferably is bromine.

As used in the specification, the straight-chain alkyl groups contain 1 to 10 carbon atoms and, in particular, are methyl, ethyl, propyl, butyl, pentyl, hexyl, heptyl, octyl, nonyl and decyl. The straight-chain alkoxy groups contain 1 to 10 carbon atoms, and in particular, are methoxy, ethoxy, propyloxy, butyloxy, pentyloxy, hexyloxy, heptyloxy, octyloxy, nonyloxy and decyloxy. The branched-chain alkyl group of the formula $C_2H_5$—$CH(CH_3)$—$(CH_2)_n$—wherein n is 1, 2 or 3, comprise 2-methylbutyl, 3-methylpentyl or 4-methylhexyl. The term "aryl" means, in particular, optionally p-substituted phenyl groups, such as for example phenyl, p-ethylphenyl, p-n-butylphenyl and the like.

The preparation of the starting materials of formulas II and III is illustrated in Formula Schemes A to D hereinafter.

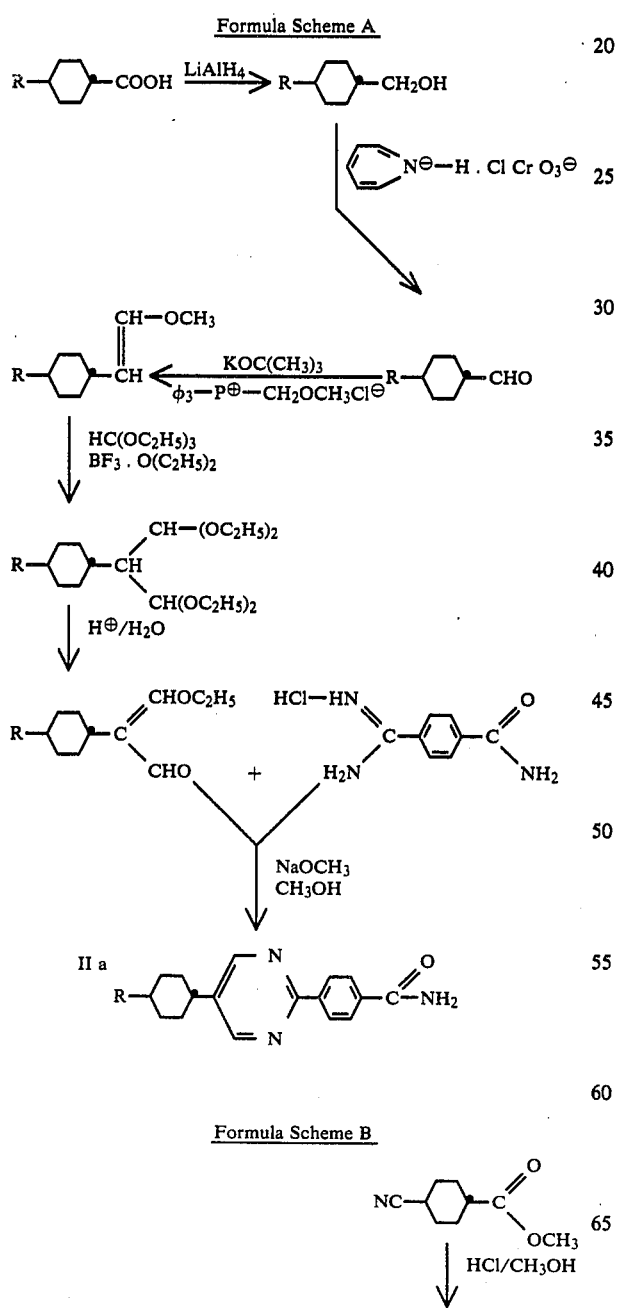
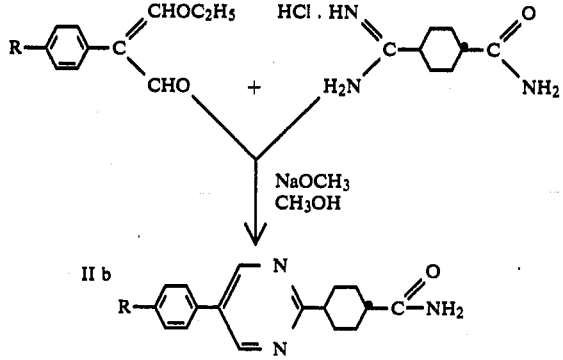
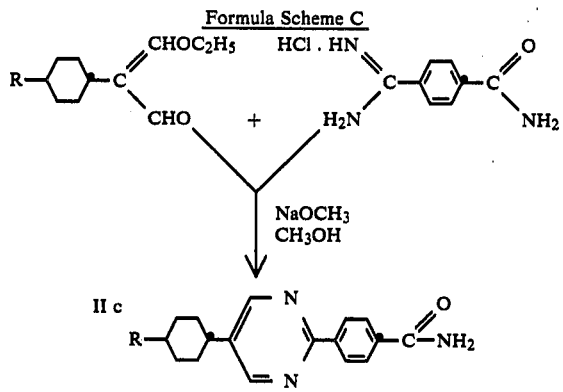
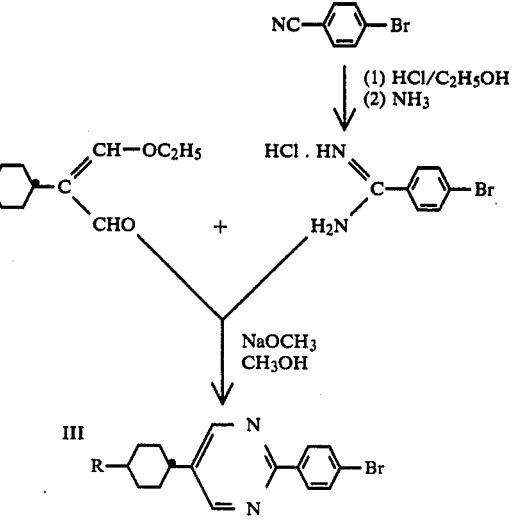

The acid starting materials wherein R is a branched-chain alkyl group as hereinbefore described can be prepared in accordance with the processes described by Gray and McDonnell in German Offenlegungsschrift No. 2,736,772 and in Mol. Cryst. Liq. Cryst. 37(1976)189.

The pyrimidine derivatives of formula I can be used in the form of mixtures with other nematic or non-nematic substances, for example, with substances from the classes of Schiffs bases, azo- or azoxybenzenes, phenyl benzoates, cyclohexane carboxylic acid phenyl esters, bi- and terphenyls, phenylcyclohexanes, cinnamic acid derivatives, phenyl- and diphenylpyrimidines or the like. Such compounds are known in the art, for example, they are described in German Offenlegungsschrifts Nos. 2,306,738; 2,306,739; 2,429,093; 2,356,085; 2,636,684; 2,459,374; 2,547,737; 2,641,724; 2,708,276; and 2,811,001. Many of such nematic or non-nematic substances are, moreover, commercially available.

The pyrimidine derivatives of formula I wherein R is a straight-chain alkyl or alkoxy group are utilized in liquid crystalline mixtures for electro-optical purposes in a weight ratio which preferably corresponds to the eutectic composition. The amount of these pyrimidine derivatives of formula I present in a liquid crystalline mixture is, however, generally in the range of from about 1 to about 50 mol percent, preferably in the range of from about 5 to about 30 mol percent.

The pyrimidine derivatives of formula I wherein R is a branched-chain alkyl group are utilized in cholesteric mixtures for electro-optical purposes in a weight ratio which is preferably given by the desired pitch of the cholesteric mixture. The amount of these pyrimidine derivatives of formula I in a cholesteric mixture containing coloring substances generally is below about 15 mol percent, preferably below about 5 mol percent. On the other hand, in the case of mixtures which do not contain a coloring substance there are often used smaller amounts, preferably, less than about 2 mol percent, of these pyrimidine derivatives.

By utilizing the pyrimidine derivatives of formula I, there can be produced mixtures which have considerable advantages over previously known mixtures. Thus, for example, the amount of pyrimidine derivatives of formula I in a mixture can be substantially higher than that of previously known compounds with similar high clearing points. This means, for example, that several pyrimidine derivatives of formula I can be combined in a mixture which leads to very high clearing points without the mixture thereby having smectic or solid crystalline tendencies. Furthermore, mixtures which contain the pyrimidine derivatives of formula I have a very slight temperature dependence of the threshold potential. This is advantageous because mixtures with a slight temperature dependence of the electro-optical transmission curves (in rotation cells) are especially well suited for multiplex working.

A further advantage of the pyrimidine derivatives of formula I is that they enable the production of mixtures having high clearing points and, nevertheless, low viscosities.

The pyrimidine derivatives of formula I can also be used in the form of liquid crystal mixtures which contain coloring substances. In order to achieve high contrasts in liquid crystal displays in which any form of the "guest-host effect" is used, it is important that the dissolved dichroic coloring substances have a high degree of order. This high degree of order depends not only on the liquid crystal matrix but also on the dichroic coloring substances which are used. Since the liquid crystal mixtures which contain one or more pyrimidine derivatives of formula I, and, if desired, additional nematic and/or non-nematic substances, have a high degree of order, they are especially suitable as the liquid crystal matrix for mixtures containing coloring substances.

Coloring substances for these mixtures, in accordance with the invention, which are preferably suitable include compounds having longish molecules and a relatively rigid molecular part, for example, azo or azoxy coloring substances, polyenes and Schiffs bases as well as, surprisingly, anthraquinone derivatives. Preferred coloring substances comprise compounds of the formulas:

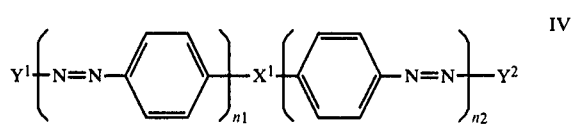

IV wherein $n_1$ and $n_2$ are zero, 1 or 2, $X^1$ is azo or azoxy, $Y^1$ and $Y^2$, which can be the same or different, are

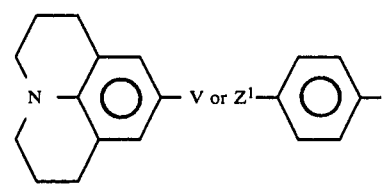

VI and $Z^1$ is hydrogen, cyano, nitro, phenyl, p-substituted phenyl, hydroxy, alkoxy, amino, dialkylamino or pyrrolidyl; or derivatives of formula IV wherein one of the benzene rings additionally carries one or more substituents selected from the group consisting of halogen, methyl, halosubstituted methyl and methoxy;

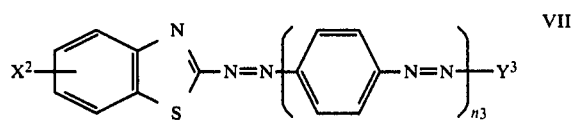

VII wherein $n_3$ is zero or 1, $Y^3$ is a group of formula V or VI hereinbefore, wherein $Z^1$ is dialkylamino or pyrrolidyl, and $X^2$ is hydrogen, halogen, cyano, nitro, alkyl, alkoxy, optionally substituted phenyl, optionally substituted benzothiazol-2-yl, alkoxycarbonyl or alkylsulfonyl in the 5- or 6-position;

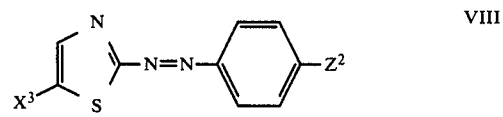

VIII wherein $X^3$ is cyano, nitro or alkyl and $Z^2$ is hydroxy, alkoxy or aryl or an optionally alkyl-substituted or aryl-substituted amino, pyrrolidyl or piperidyl; or derivatives of formula VIII wherein the benzene ring additionally carries one or more substituents selected from the group consisting of halogen, hydroxy, methyl and methoxy;

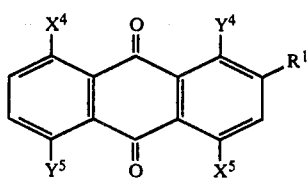 IX wherein $X^4$ and $X^5$ are hydroxy, $Y^4$ and $Y^5$ are amino and $R^1$ is a group of formula VI hereinbefore or $X^4$, $Y^5$ and $R^1$ are each hydrogen, $X^5$ is hydroxy and $Y^4$ is the group $-NHR^2$ or $X^4$, $X^5$ and $R^1$ are each hydrogen and $Y^4$ and $Y^5$ are each $-NHR^2$, $R^2$ is a group of formula VI hereinbefore wherein $Z^1$ is alkyl, alkoxy or dialkylamino;

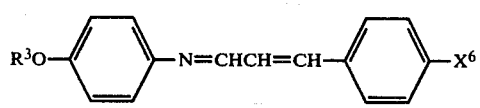 X wherein $R^3$ is alkyl and $X^6$ is cyano or nitro;

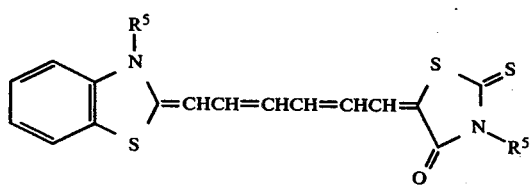 XI wherein $R^4$ is alkyl; and

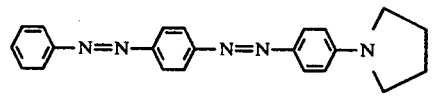 XII
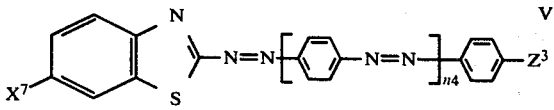

wherein $R^5$ is alkyl.

The foregoing compounds are known compounds or are analogs of known compounds.

The following compounds are especially preferred coloring substances:

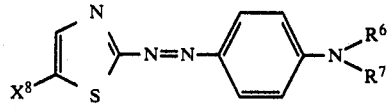 IVa

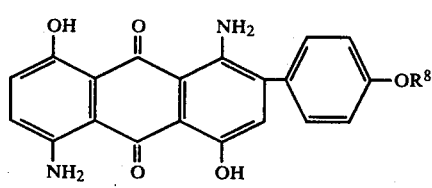 VIIa wherein $n_4$ is zero or 1, $Z^3$ is dimethylamino or diethylamino and $X^7$ is hydrogen, methyl, ethoxy, n-butyloxy, nitro or n-butylsulfonyl;

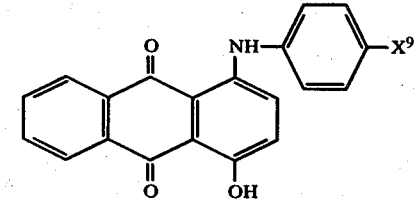 VIIIa wherein $R^6$, $R^7$ and $X^8$ are each methyl or $R^6$ is methyl, $X^8$ is nitro and $R^7$ is methyl, phenyl or p-n-butylphenyl;

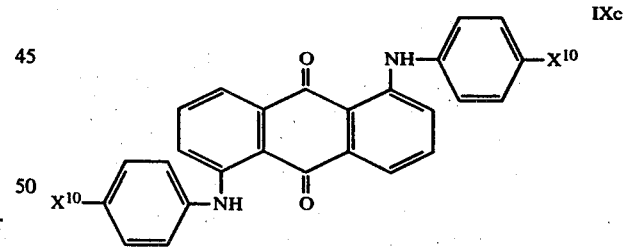 IXa wherein $R^8$ is n-alkyl containing 1 to 10 carbon atoms;

IXb wherein $X^9$ is n-butyl, n-nonyloxy or dimethylamino;

IXc wherein $X^{10}$ is ethyl, n-butyl, isopropyl, pentyloxy or dimethylamino; the compound of formula X wherein $R^3$ is n-butyl and $X^6$ is nitro; the compound of formula XI wherein $R^4$ is ethyl; and the compound of formula XII wherein $R^5$ is ethyl.

The mixtures, in accordance with the invention, which contain coloring substances can contain 1 to about 4 coloring substances. The amount of coloring substance in a liquid crystalline mixture, in the case of anthraquinones, is in the range of from about 0.2 to about 3 weight percent, preferably in the range of from about 1 to about 2 weight percent, and, in the case of the customary coloring substances, is in the range of from about 0.1 to about 2 weight percent, preferably in the range of from about 0.5 to about 1 weight percent.

The preparation of mixtures which contain, inter alia, pyrimidine derivatives of formula I as well as other nematic and/or non-nematic compounds and/or one or more coloring substances can be carried out in a known manner; for example, by heating a mixture of the components to a temperature barely above the clearing point and, subsequently, cooling the mixture down.

Examples of preferred mixtures are given hereinafter. The percentages are expressed in mol percent unless expressly stated to the contrary and S denotes the degree of order.

Mixture 1:
19% trans-p-(4-propylcyclohexyl)benzonitrile,
34% trans-p-(4-pentylcyclohexyl)benzonitrile,
22% trans-p-(4-heptylcyclohexyl)benzonitrile,
3% trans-4-[5-(p-butylphenyl)-2-pyrimidinyl]cyclohexane carbonitrile,
10% trans-4-[5-(p-hexylphenyl)-2-pyrimidinyl]cyclohexane carbonitrile, and
12% trans-4-[5-(p-octylphenyl)-2-pyrimidinyl]cyclohexane carbonitrile, melting point <0° C.; clearing point 77° C.

Mixture 2:
16% trans-4-propylcyclohexane carboxylic acid p-cyanophenyl ester,
9.5% trans-4-butylcyclohexane carboxylic acid p-cyanophenyl ester,
14.5% trans-4-pentylcyclohexane carboxylic acid p-cyanophenyl ester,
8% p-butylbenzoic acid p'-cyanophenyl ester,
8% p-(5-pentyl-2-pyrimidinyl)benzonitrile,
15% p-(5-heptyl-2-pyrimidinyl)benzonitrile,
12% trans-p-[5-(4-ethylcyclohexyl)-2-pyrimidinyl]benzonitrile, and
17% trans-p-[5-(4-heptylcyclohexyl)-2-pyrimidinyl]benzonitrile, melting point <0° C.; clearing point 109° C.

Mixture 3:
8% p-(5-pentyl-2-pyrimidinyl)benzonitrile,
14% p-(5-heptyl-2-pyrimidinyl)benzonitrile,
9% 4'-octyloxy-4-cyanobiphenyl,
40% trans-p-(4-pentylcyclohexyl)benzonitrile,
12% trans-p-[5-(4-ethylcyclohexyl)-2-pyrimidinyl]benzonitrile, and
17% trans-p-[5-(4-heptylcyclohexyl)-2-pyrimidinyl]benzonitrile, melting point <0° C.; clearing point 102° C.

Mixture 4:
8% p-(4-pentyl-2-pyrimidinyl)benzonitrile,
12% p-(5-heptyl-2-pyrimidinyl)benzonitrile,
46% 4'-pentyl-4-cyanobiphenyl,
8% 4'-octyloxy-4-cyanobiphenyl,
11% trans-p-[5-(4-ethylcyclohexyl)-2-pyrimidinyl]benzonitrile, and
15% trans-p-[5-(4-heptylcyclohexyl)-2-pyrimidinyl]benzonitrile, melting point <0° C.; clearing point 94° C.

Mixture 5:
5% p-butylbenzoic acid p'-cyanophenyl ester,
6% p-(5-pentyl-2-pyrimidinyl)benzonitrile,
43% 4'-pentyl-4-cyanobiphenyl,
12% trans-4-propylcyclohexane carboxylic acid p-cyanophenyl ester,
7% trans-4-butylcyclohexane carboxylic acid p-cyanophenyl ester,
11% trans-4-pentylcyclohexane carboxylic acid p-cyanophenyl ester,
11% trans-p-[5-(4-ethylcyclohexyl)-2-pyrimidinyl]benzonitrile, and
5% trans-p-[5-(4-propylcyclohexyl)-2-pyrimidinyl]benzonitrile, melting point <0° C.; clearing point 75° C.

Mixture 6:
7% p-(5-pentyl-2-pyrimidinyl)benzonitrile,
46% 4'-pentyl-4-cyanobiphenyl,
8% trans-4-butylcyclohexane carboxylic acid p-cyanophenyl ester,
12% trans-4-pentylcyclohexane carboxylic acid p-cyanophenyl ester,
11% trans-p-[5-(4-ethylcyclohexyl)-2-pyrimidinyl]benzonitrile, and
16% trans-p-[5-(4-heptylcyclohexyl)-2-pyrimidinyl]benzonitrile, melting point <0° C.; clearing point 97° C.

Mixture 7:
8% p-(5-pentyl-2-pyrimidinyl)benzonitrile,
51% 4'-pentyl-4-cyanobiphenyl,
9% trans-4-butylcyclohexane carboxylic acid p-cyanophenyl ester,
14% trans-4-pentylcyclohexane carboxylic acid p-cyanophenyl ester,
12% trans-p-[5-(4-ethylcyclohexyl)-2-pyrimidinyl]benzonitrile, and
6% trans-p-[5-(4-propylcyclohexyl)-2-pyrimidinyl]benzonitrile, melting point <0° C.; clearing point 78° C.

Mixture 8:
9% p-(5-pentyl-2-pyrimidinyl)benzonitrile,
55% 4'-pentyl-4-cyanobiphenyl,
16% trans-5-pentylcyclohexane carboxylic acid p-cyanophenyl ester,
13% trans-p-[5-(4-ethylcyclohexyl)-2-pyrimidinyl]benzonitrile, and
7% trans-p-[5-(4-propylcyclohexyl)-2-pyrimidinyl]benzonitrile, melting point <0° C.; clearing point 80° C.

Mixture 9:
8% p-(5-pentyl-2-pyrimidinyl)benzonitrile,
14% p-(5-heptyl-2-pyrimidinyl)benzonitrile,
50% 4'-pentyl-4-cyanobiphenyl,
10% 4'-octyloxy-4-cyanobiphenyl,
12% trans-p-[5-(4-ethylcyclohexyl)-2-pyrimidinyl]benzonitrile, and
6% trans-p-[5-(4-propylcyclohexyl)-2-pyrimidinyl]benzonitrile, melting point <0° C.; clearing point 77° C.

Mixture 10:
7% p-butylbenzoic acid p'-cyanophenyl ester,
7% p-(5-pentyl-2-pyrimidinyl)benzonitrile,
39% trans-p-(4-pentylcyclohexyl)benzonitrile,
15% trans-4-propylcyclohexane carboxylic acid p-cyanophenyl ester,
14% trans-4-pentylcyclohexane carboxylic acid p-cyanophenyl ester,
12% trans-p-[5-(4-ethylcyclohexyl)-2-pyrimidinyl]benzonitrile, and
6% trans-p-[5-(4-propylcyclohexyl)-2-pyrimidinyl]benzonitrile, melting point <20° C.; clearing point 90° C.

Mixture 11:
6% p-butylbenzoic acid p'-cyanophenyl ester,
7% p-(5-pentyl-2-pyrimidinyl)benzonitrile,
38% trans-p-(4-pentylcyclohexyl)benzonitrile,
14% trans-4-propylcyclohexane carboxylic acid p-cyanophenyl ester, 12% trans-4-pentylcyclohexane carboxylic acid p-cyanophenyl ester,
11.5% p-[5-(4-butylphenyl)-2-pyrimidinyl]benzonitrile, and
11.5% trans-p-[5-(4-ethylcyclohexyl)-2-pyrimidinyl]benzonitrile, melting point <20° C.; clearing point 94° C.

Mixture 12:
4% p-butylbenzoic acid p'-cyanophenyl ester,
4% p-(5-pentyl-2-pyrimidinyl)benzonitrile,
8% p-(5-heptyl-2-pyrimidinyl)benzonitrile,
35% 4'-pentyl-4-cyanobiphenyl,
27% trans-p-(4-pentylcyclohexyl)benzonitrile,
5% trans-4-butylcyclohexane carboxylic acid p-cyanophenyl ester,
8% p-[5-(4-butylphenyl)-2-pyrimidinyl]benzonitrile, and
9% trans-p-[5-(4-ethylcyclohexyl)-2-pyrimidinyl]benzonitrile, melting point <−10° C.; clearing point 72° C.

Mixture 13:
5% p-(5-pentyl-2-pyrimidinyl)benzonitrile,
9% p-(5-heptyl-2-pyrimidinyl)benzonitrile,
38% 4'-pentyl-4-cyanobiphenyl,
30% trans-p-(4-pentylcyclohexyl)benzonitrile,
9% p-[5-(4-butylphenyl)-2-pyrimidinyl]benzonitrile, and
9% trans-p-[5-(4-ethylcyclohexyl)-2-pyrimidinyl]benzonitrile, melting point <−10° C.; clearing point 75° C.

Mixture 14:
5% p-(5-pentyl-2-pyrimidinyl)benzonitrile,
9% p-(5-heptyl-2-pyrimidinyl)benzonitrile,
38% 4'-pentyl-4-cyanobiphenyl,
10.4% trans-4-propylcyclohexane carboxylic acid p-cyanophenyl ester,
5.6% trans-4-butylcyclohexane carboxylic acid p-cyanophenyl ester,
9% trans-4-pentylcyclohexane carboxylic acid p-cyanophenyl ester,
10% trans-p-[5-(4-ethylcyclohexyl)-2-pyrimidinyl]benzonitrile, and
13% trans-p-[5-(4-heptylcyclohexyl)-2-pyrimidinyl]benzonitrile, melting point <−10° C.; clearing point 91° C.

Mixture 15:
5.5% p-(5-pentyl-2-pyrimidinyl)benzonitrile,
10% p-(5-heptyl-2-pyrimidinyl)benzonitrile,
33% trans-p-(4-pentylcyclohexyl)benzonitrile,
11.5% trans-4-propylcyclohexane carboxylic acid p-cyanophenyl ester,
6% trans-4-butylcyclohexane carboxylic acid p-cyanophenyl ester,
10% trans-4-pentylcyclohexane carboxylic acid p-cyanophenyl ester,
10% trans-p-[5-(4-ethylcyclohexyl)-2-pyrimidinyl]benzonitrile, and
14% trans-p-[5-(4-heptylcyclohexyl)-2-pyrimidinyl]benzonitrile, melting point <−10° C.; clearing point 98° C.

Mixture 16:
7% p-(5-pentyl-2-pyrimidinyl)benzonitrile,
13% p-(5-heptyl-2-pyrimidinyl)benzonitrile,
47% 4'-pentyl-4-cyanobiphenyl,
9% 4'-octyloxy-4-cyanobiphenyl,
8% 4''-pentyl-cyano-p-terphenyl, and
16% trans-p-[B 5-(4-heptylcyclohexyl)-2-pyrimidinyl]benzonitrile, melting point <0° C.; clearing point 95° C.

Mixture 17:
5% p-butylbenzoic acid p'-cyanophenyl ester,
5% p-(5-pentyl-2-pyrimidinyl)benzonitrile,
40% 4'-pentyl-4-cyanobiphenyl,
11% trans-4-propylcyclohexane carboxylic acid p-cyanophenyl ester,
6% trans-4-butylcyclohexane carboxylic acid p-cyanophenyl ester,
9% trans-4-pentylcyclohexane carboxylic acid p-cyanophenyl ester,
10% trans-p-[5-(4-ethylcyclohexyl)-2-pyrimidinyl]benzonitrile, and
14% trans-p-[5-(4-heptylcyclohexyl)-2-pyrimidinyl]benzonitrile, melting point <−10° C.; clearing point 93° C.

Mixture 18:
6.5% p-(5-pentyl-2-pyrimidinyl)benzonitrile,
12% p-(5-heptyl-2-pyrimidinyl)benzonitrile,
47% 4'-pentyl-4-cyanobiphenyl,
8% 4'-octyloxy-4-cyanobiphenyl,
11% p-[5-(4-butylphenyl)-2-pyrimidinyl]benzonitrile, and
15.5% trans-p-[5-(4-heptylcyclohexyl)-2-pyrimidinyl]benzonitrile, melting point <0° C.; clearing point 98° C.

Mixture 19:
6% p-(5-pentyl-2-pyrimidinyl)benzonitrile,
42% 4'-pentyl-4-cyanobiphenyl,
7% trans-4-butylcyclohexane carboxylic acid p-cyanophenyl ester,
10% trans-4-pentylcyclohexane carboxylic acid p-cyanophenyl ester,
10% p-[5-(4-butylphenyl)-2-pyrimidinyl]benzonitrile,
10.5% trans-p-[5-(4-ethylcyclohexyl)-2-pyrimidinyl]benzonitrile, and
14.5% trans-p-[5-(4-heptylcyclohexyl)-2-pyrimidinyl]benzonitrile, melting point <0° C.; clearing point 112° C.

Mixture 20:
8.1% p-(5-pentyl-2-pyrimidinyl)benzonitrile,
15.1% p-(5-heptyl-2-pyrimidinyl)benzonitrile,
16.2% trans-4-propylcyclohexane carboxylic acid p-cyanophenyl ester,
9.7% trans-4-butylcyclohexane carboxylic acid p-cyanophenyl ester,
14.8% trans-4-pentylcyclohexane carboxylic acid p-cyanophenyl ester,
23.6% trans-4-pentylcyclohexane carboxylic acid p-methoxyphenyl ester, and
12.5% trans-p-[5-(4-ethylcyclohexyl)-2-pyrimidinyl]benzonitrile, melting point <0° C.; clearing point 76° C.

Mixture 21:
7% p-butylbenzoic acid p'-cyanophenyl ester,
8% p-(5-pentyl-2-pyrimidinyl)benzonitrile,
53% 4'-pentyl-4-cyanobiphenyl,
14% trans-4-pentylcyclohexane carboxylic acid p-cyanophenyl ester,
12% trans-p-[5-(4-ethylcyclohexyl)-2-pyrimidinyl]benzonitrile, and
6% trans-p-[5-(4-propylcyclohexyl)-2-pyrimidinyl]benzonitrile, melting point <0° C.; clearing point 77° C.

Mixture 22:
5% p-(5-pentyl-2-pyrimidinyl)benzonitrile,

10% p-(5-heptyl-2-pyrimidinyl)benzonitrile,
40% 4'-pentyl-4-cyanobiphenyl,
30% trans-p-(4-pentylcyclohexyl)benzonitrile,
10% trans-p-[5-(4-ethylcyclohexyl)-2-pyrimidinyl]-benzonitrile, and
5% trans-p-[5-(4-propylcyclohexyl)-2-pyrimidinyl]benzonitrile, melting point < −10° C.; clearing point 70° C.

Mixture 23:
42% 4'-pentyl-4-cyanobiphenyl,
33% trans-p-(4-pentylcyclohexyl)benzonitrile,
10.5% p-[5-(4-butylphenyl)-2-pyrimidinyl]benzonitrile,
10% trans-p-[5-(4-ethylcyclohexyl)-2-pyrimidinyl]-benzonitrile, and
4.5% trans-p-[5-(4-propylcyclohexyl)-2-pyrimidinyl]-benzonitrile, melting point < −10° C.; clearing point 87° C.

Mixture 24:
5% p-butylbenzoic acid p'-cyanophenyl ester,
6% p-(5-pentyl-2-pyrimidinyl)benzonitrile,
11% p-(5-heptyl-2-pyrimidinyl)benzonitrile,
12% trans-4-propylcyclohexane carboxylic acid p-cyanophenyl ester,
7% trans-4-butylcyclohexane carboxylic acid p-cyanophenyl ester,
10% trans-4-pentylcyclohexane carboxylic acid p-cyanophenyl ester,
24% trans-4-pentylcyclohexane carboxylic acid p-(propyloxy)phenyl ester
10.5% trans-p-[5-(4-ethylcyclohexyl)-2-pyrimidinyl]-benzonitrile, and
14.5% trans-p-[5-(4-heptylcyclohexyl)-2-pyrimidinyl]benzonitrile, melting point <5° C.; clearing point 99° C.

Mixture 25:
5% p-butylbenzoic acid p'-cyanophenyl ester,
6% p-[5-pentyl-2-pyrimidinyl]benzonitrile,
11% p-[5-heptyl-2-pyrimidinyl]benzonitrile,
12% trans-4-propylcyclohexane carboxylic acid p-cyanophenyl ester,
7% trans-4-butylcyclohexane carboxylic acid p-cyanophenyl ester,
10% trans-4-pentylcyclohexane carboxylic acid p-cyanophenyl ester,
24% trans-4-pentylcyclohexane carboxylic acid p-(propyloxy)phenyl ester
10.5% p-[5-(4-butylphenyl)-2-pyrimidinyl]benzonitrile, and
14.5% trans-p-[5-(4-heptylcyclohexyl)-2-pyrimidinyl]benzonitrile, melting point <20° C.; clearing point 102° C.

Mixture 26:
4.4% p-(5-Pentyl-2-pyrimidinyl)benzonitrile,
7.8% p-(5-heptyl-2-pyrimidinyl)benzonitrile,
35.6% 4'-pentyl-4-cyanobiphenyl,
9.3% trans-4-propylcyclohexane carboxylic acid p-cyanophenyl ester,
7.7% trans-4-pentylcyclohexane carboxylic acid p-cyanophenyl ester,
21.0% trans-4-butylcyclohexane carboxylic acid p-(hexyloxy)phenyl ester,
8.8% trans-p-[5-(4-ethylcyclohexyl)-2-pyrimidinyl]-benzonitrile, and
5.4% trans-p-[5-(4-heptylcyclohexyl)-2-pyrimidinyl]-benzonitrile, melting point < −10° C.; clearing point 72° C.

Mixture 27:
4.4% p-(5-Pentyl-2-pyrimidinyl)benzonitrile,
35.3% 4'-pentyl-4-cyanobiphenyl,
9.7% trans-4-propylcyclohexane carboxylic acid p-cyanophenyl ester,
7.7% trans-4-pentylcyclohexane carboxylic acid p-cyanophenyl ester,
13.6% trans-4-pentylcyclohexane carboxylic acid p-(methoxy)phenyl ester,
8.5% 2-(4-cyanophenyl)-5-(4-butylphenyl)pyrimidine,
8.8% trans-p-[5-(4-ethylcyclohexyl)-2-pyrimidinyl]-benzonitrile, and
12.0% trans-p-[5-(4-heptylcyclohexyl)-2-pyrimidinyl]benzonitrile, melting point < −10° C.; clearing point 104° C.

Mixture 28:
38.2% 4'-Pentyl-4-cyanobiphenyl,
4.9% p-(5-pentyl-2-pyrimidinyl)benzonitrile,
8.8% p-(5-heptyl-2-pyrimidinyl)benzonitrile,
10.3% trans-4-propylcyclohexane carboxylic acid p-cyanophenyl ester,
8.7% trans-4-pentylcyclohexane carboxylic acid p-cyanophenyl ester,
23.2% trans-4-butylcyclohexane carboxylic acid p-(hexyloxy)phenyl ester,
2.9% trans-4-[5-(4-propylphenyl)-2-pyrimidinyl]cyclohexane carbonitrile, and
3.1% trans-4-[5-(4-pentylphenyl)-2-pyrimidinyl]cyclohexane carbonitrile, melting point < −10° C.; clearing point 57° C.

Mixture 29:
35.5% 4'-Pentyl-4-cyanobiphenyl,
4.4% p-(5-pentyl-2-pyrimidinyl)benzonitrile,
7.8% p-(5-heptyl-2-pyrimidinyl)benzonitrile,
9.3% trans-4-propylcyclohexane carboxylic acid p-cyanophenyl ester,
7.7% trans-4-pentylcyclohexane carboxylic acid p-cyanophenyl ester,
20.8% trans-4-butylcyclohexane carboxylic acid p-(hexyloxy)phenyl ester,
4.0% trans-p-[5-(4-propylcyclohexyl)-2-pyrimidinyl]-benzonitrile, and
10.5% trans-4-[5-(4-heptylphenyl)-2-pyrimidinyl]cyclohexane carbonitrile, melting point < −10° C.; clearing point 68° C.

Mixture 30:
37.0% 4'-Pentyl-4-cyanobiphenyl,
10.0% trans-4-propylcyclohexane carboxylic acid p-cyanophenyl ester,
8.0% trans-4-pentylcyclohexane carboxylic acid p-cyanophenyl ester,
14.0% trans-4-pentylcyclohexane carboxylic acid p-(methoxy)phenyl ester,
9.0% 2-(4-cyanophenyl)-5-(4-butylphenyl)pyrimidine,
9.0% trans-p-[5-(4-ethylcyclohexyl)-2-pyrimidinyl]-benzonitrile,
13.0% trans-p-[5-(4-heptylcyclohexyl)-2-pyrimidinyl]benzonitrile, melting point < −10° C.; clearing point 106° C.

Mixture 31:
38.0% 4'-Pentyl-4-cyanobiphenyl,
10.0% trans-4-propylcyclohexane carboxylic acid p-cyanophenyl ester,
9.0% trans-4-pentylcyclohexane carboxylic acid p-cyanophenyl ester,
15.0% trans-4-pentylcyclohexane carboxylic acid p-(methoxy)phenyl ester, 9.0% trans-p-[5-(4-ethylcyclohexyl)-2-pyrimidinyl]-benzonitrile,
6.0% trans-p-[5-(4-pentylcyclohexyl)-2-pyrimidinyl]-benzonitrile, and
13.0% trans-p-[5-(4-heptylcyclohexyl)-2-pyrimidinyl]benzonitrile, melting point < −10° C.; clearing point 102° C.

Mixture 32:
6.4% p-(5-Pentyl-2-pyrimidinyl)benzonitrile,
11.9% p-(5-heptyl-2-pyrimidinyl)benzonitrile,
7.5% trans-4-butylcyclohexane carboxylic acid p-cyanophenyl ester,
11.6% trans-4-pentylcyclohexane carboxylic acid p-cyanophenyl ester,
19.3% trans-4-pentylcyclohexane carboxylic acid p-(methoxy)phenyl ester,
26.2% trans-4-pentylcyclohexane carboxylic acid p-(propyloxy)phenyl ester,
11.1% trans-p-[5-(4-ethylcyclohexyl)-2-pyrimidinyl]-benzonitrile, and
6.0% trans-p-[5-(4-butylcyclohexyl)-2-pyrimidinyl]-benzonitrile, melting point <10° C.; clearing point 83° C.

Mixture 33:
5.0% p-(5-Pentyl-2-pyrimidinyl)benzonitrile,
9.2% p-(5-heptyl-2-pyrimidinyl)benzonitrile,
39.1% 4'-pentyl-4-cyanobiphenyl,
5.7% trans-4-butylcyclohexane carboxylic acid p-cyanophenyl ester,
9.1% trans-4-pentylcyclohexane carboxylic acid p-cyanophenyl ester,
22.2% trans-4-pentylcyclohexane carboxylic acid p-(propyloxy)phenyl ester, and
9.7% trans-p-[5-(4-ethylcyclohexyl)-2-pyrimidinyl]-benzonitrile, melting point <0° C.; clearing point 64° C.

Mixture 34:
4.7% p-(5-Pentyl-2-pyrimidinyl)benzonitrile,
8.5% p-(5-heptyl-2-pyrimidinyl)benzonitrile,
37.7% 4'-pentyl-4-cyanobiphenyl,
5.3% trans-4-butylcyclohexane carboxylic acid p-cyanophenyl ester,
8.4% trans-4-pentylcyclohexane carboxylic acid p-cyanophenyl ester,
21.3% trans-4-pentylcyclohexane carboxylic acid p-(propyloxy)phenyl ester,
9.3% trans-p-[5-(4-ethylcyclohexyl)-2-pyrimidinyl]-benzonitrile, and
4.8% trans-p-[5-(4-butylcyclohexyl)-2-pyrimidinyl]-benzonitrile, melting point <0° C.; clearing point 71° C.

Mixture 35:
34.0% 4'-Pentyl-4-cyanobiphenyl,
5.0% trans-4-butylcyclohexane carboxylic acid p-cyanophenyl ester,
8.0% trans-4-pentylcyclohexane carboxylic acid p-cyanophenyl ester,
13.0% trans-4-pentylcyclohexane carboxylic acid p-(methoxy)phenyl ester,
19.0% trans-4-pentylcyclohexane carboxylic acid p-(propyloxy)phenyl ester,
9.0% trans-p-[5-(4-ethylcyclohexyl)-2-pyrimidinyl]-benzonitrile,
4.0% trans-p-[5-(4-butylcyclohexyl)-2-pyrimidinyl]-benzonitrile, and
8.0% trans-p-[5-(4-pentylcyclohexyl)-2-pyrimidinyl]-benzonitrile, melting point < −10° C.; clearing point 87° C.

Mixture 36:
40.0% 4'-Pentyl-4-cyanobiphenyl,
7.0% 4'-octyloxy-4-cyanobiphenyl,
5.0% p-(5-pentyl-2-pyrimidinyl)benzonitrile,
10.0% p-(5-heptyl-2-pyrimidinyl)benzonitrile,
23.0% trans-4-pentylcyclohexane carboxylic acid p-(propyloxy)phenyl ester,
10.0% trans-p-[5-(4-ethylcyclohexyl)-2-pyrimidinyl]-benzonitrile,
5.0% trans-p-[5-(4-butylcyclohexyl)-2-pyrimidinyl]-benzonitrile, melting point <0° C.; clearing point 72° C.

Mixture 37:
35.0% 4'-Pentyl-4-cyanobiphenyl,
19.0% 4'-pentyloxy-4-cyanobiphenyl,
4.0% p-(5-pentyl-2-pyrimidinyl)benzonitrile,
8.0% p-(5-heptyl-2-pyrimidinyl)benzonitrile,
20.0% trans-4-pentylcyclohexane carboxylic acid p-(propyloxy)phenyl ester,
9.0% trans-p-[5-(4-ethylcyclohexyl-2-pyrimidinyl)-benzonitrile, and
5.0% trans-p-[5-(4-butylcyclohexyl)-2-pyrimidinyl]-benzonitrile, melting point <10° C.; clearing point 73° C.

Mixture 38:
7.0% p-Butylbenzoic acid p'-cyanophenyl ester,
8.0% p-(5-pentyl-2-pyrimidinyl)benzonitrile,
15.0% p-(5-heptyl-2-pyrimidinyl)benzonitrile,
10.0% trans-4-butylcyclohexane carboxylic acid p-cyanophenyl ester,
14.0% trans-4-pentylcyclohexane carboxylic acid p-cyanophenyl ester,
25.0% trans-4-butylcyclohexane carboxylic acid p-(ethoxy)phenyl ester,
13.0% trans-p-[5-(4-ethylcyclohexyl)-2-pyrimidinyl]-benzonitrile, and
8.0% trans-p-[5-(4-pentylcyclohexyl)-2-pyrimidinyl]-benzonitrile, melting point <10° C.; clearing point 88° C.

Mixture 39:
5.0% p-Butylbenzoic acid p'-cyanophenyl ester,
6.0% p-(5-pentyl-2-pyrimidinyl)benzonitrile,
10.0% p-(5-heptyl-2-pyrimidinyl)benzonitrile,
7.0% trans-4-butylcyclohexane carboxylic acid p-cyanophenyl ester,
11.0% trans-4-pentylcyclohexane carboxylic acid p-cyanophenyl ester,
19.0% trans-4-butylcyclohexane carboxylic acid p-(ethoxy)phenyl ester,
20.0% 4'-heptyl-4-cyanobiphenyl,
10.0% trans-p-[5-(4-ethylcyclohexyl)-2-pyrimidinyl]-benzonitrile,
5.0% trans-p-[5-(4-butylcyclohexyl)-2-pyrimidinyl]-benzonitrile, and
7.0% trans-p-[5-(4-pentylcyclohexyl)-2-pyrimidinyl]-benzonitrile, melting point <0° C.; clearing point 89° C.

Mixture 40:
19.0% 4'-Heptyl-4-cyanobiphenyl,
5.0% p-butylbenzoic acid p'-cyanophenyl ester,
6.0% p-(5-pentyl-2-pyrimidinyl)benzonitrile,
10.0% p-(5-heptyl-2-pyrimidinyl)benzonitrile,
7.0% trans-4-butylcyclohexane carboxylic acid p-cyanophenyl ester,
10.0% trans-4-pentylcyclohexane carboxylic acid p-cyanophenyl ester,
19.0% trans-4-butylcyclohexane carboxylic acid p-(ethoxy)phenyl ester, 10.0% trans-p-[5-(4-ethylcyclohexyl)-2-pyrimidinyl]-benzonitrile, and 14.0% trans-p-[5-(4-heptylcyclohexyl)-2-pyrimidinyl]benzonitrile, melting point <0° C.; clearing point 93° C.

Mixture 41:
4.0% p-Butylbenzoic acid p'-cyanophenyl ester,
5.0% p-(5-pentyl-2-pyrimidinyl)benzonitrile,
9.0% p-(5-heptyl-2-pyrimidinyl)benzonitrile,
29.0% trans-p-(4-pentylcyclohexyl)benzonitrile,
6.0% trans-4-butylcyclohexane carboxylic acid p-cyanophenyl ester,
9.0% trans-4-pentylcyclohexane carboxylic acid p-cyanophenyl ester,
16.0% trans-4-butylcyclohexane carboxylic acid p-(ethoxy)phenyl ester,
9.0% trans-p-[5-(4-ethylcyclohexyl)-2-pyrimidinyl]-benzonitrile, and
13.0% trans-p-[5-(4-heptylcyclohexyl)-2-pyrimidinyl]benzonitrile, melting point < −10° C.; clearing point 93° C.

Mixture 42:
16.0% 4'-Heptyl-4-cyanobiphenyl,
4.0% p-butylbenzoic acid p'-cyanophenyl ester,
5.0% p-(5-pentyl-2-pyrimidinyl)benzonitrile,
9.0% p-(5-heptyl-2-pyrimidinyl)benzonitrile,
5.0% trans-4-butylcyclohexane carboxylic acid p-cyanophenyl ester,
9.0% trans-4-pentylcyclohexane carboxylic acid p-cyanophenyl ester,
16.0% trans-4-butylcyclohexane carboxylic acid p-(ethoxy)phenyl ester,
15.0% trans-4-pentylcyclohexane carboxylic acid p-(methoxy)phenyl ester,
9.0% trans-p-[5-(4-ethylcyclohexyl)-2-pyrimidinyl]-benzonitrile, and
12.0% trans-p-[5-(4-heptylcyclohexyl)-2-pyrimidinyl]benzonitrile, melting point < −10° C.; clearing point 89° C.

Mixture 43:
8.0% p-Butylbenzoic acid p'-cyanophenyl ester,
9.0% p-(5-pentyl-2-pyrimidinyl)benzonitrile,
16.0% p-(5-heptyl-2-pyrimidinyl)benzonitrile,
10.0% trans-4-butylcyclohexane carboxylic acid p-cyanophenyl ester,
16.0% trans-4-pentylcyclohexane carboxylic acid p-cyanophenyl ester,
27.0% trans-4-butylcyclohexane carboxylic acid p-(ethoxy)phenyl ester, and
14.0% trans-p-[5-(4-ethylcyclohexyl)-2-pyrimidinyl]-benzonitrile, melting point <10° C.; clearing point 77° C.

Mixture 44:
7.0% p-Butylbenzoic acid p'-cyanophenyl ester,
8.0% p-(5-pentyl-2-pyrimidinyl)benzonitrile,
15.0% p-(5-heptyl-2-pyrimidinyl)benzonitrile,
10.0% trans-4-butylcyclohexane carboxylic acid p-cyanophenyl ester,
14.0% trans-4-pentylcyclohexane carboxylic acid p-cyanophenyl ester,
26.0% trans-4-butylcyclohexane carboxylic acid p-(ethoxy)phenyl ester,
8.0% trans-p-[5-(4-ethylcyclohexyl)-2-pyrimidinyl]-benzonitrile, and
12.0% trans-p-[5-(4-pentylcyclohexyl)-2-pyrimidinyl]benzonitrile, melting point <0° C.; clearing point 91° C.

Mixture 45:
6.0% p-Butylbenzoic acid p'-cyanophenyl ester,
7.0% p-(5-pentyl-2-pyrimidinyl)benzonitrile,
13.0% p-(5-heptyl-2-pyrimidinyl)benzonitrile,
8.0% trans-4-butylcyclohexane carboxylic acid p-cyanophenyl ester,
12.0% trans-4-pentylcyclohexane carboxylic acid p-cyanophenyl ester,
22.0% trans-4-butylcyclohexane carboxylic acid p-(ethoxy)phenyl ester,
20.0% trans-4-pentylcyclohexane carboxylic acid p-(methoxy)phenyl ester, and
12.0% trans-p-[5-(4-ethylcyclohexyl)-2-pyrimidinyl]-benzonitrile, melting point <10° C.; clearing point 74° C.

Mixture 46:
5.0% p-Butylbenzoic acid p'-cyanophenyl ester,
6.0% p-(5-pentyl-2-pyrimidinyl)benzonitrile,
10.0% p-(5-heptyl-2-pyrimidinyl)benzonitrile,
12.0% trans-4-propylcyclohexane carboxylic acid p-cyanophenyl ester,
10.0% trans-4-pentylcyclohexane carboxylic acid p-cyanophenyl ester,
19.0% trans-4-butylcyclohexane carboxylic acid p-(ethoxy)phenyl ester,
17.0% trans-4-pentylcyclohexane carboxylic acid p-(methoxy)phenyl ester,
7.0% trans-p-[5-(4-pentylcyclohexyl)-2-pyrimidinyl]-benzonitrile, and
14.0% trans-p-[5-(4-heptylcyclohexyl)-2-pyrimidinyl]benzonitrile, melting point <0° C.; clearing point 97° C.

Mixture 47:
6.0% p-butylbenzoic acid p'-cyanophenyl ester,
6.0% p-(5-pentyl-2-pyrimidinyl)benzonitrile,
12.0% p-(5-heptyl-2-pyrimidinyl)benzonitrile,
13.0% trans-4-propylcyclohexane carboxylic acid p-cyanophenyl ester,
12.0% trans-4-pentylcyclohexane carboxylic acid p-cyanophenyl ester,
21.0% trans-4-butylcyclohexane carboxylic acid p-(ethoxy)phenyl ester,
19.0% trans-4-pentylcyclohexane carboxylic acid p-(methoxy)phenyl ester, and
11.0% trans-p-[5-(4-ethylcyclohexyl)-2-pyrimidinyl]-benzonitrile, melting point <0° C.; clearing point 74° C.

Mixture 48:
6.0% p-Butylbenzoic acid p'-cyanophenyl ester,
6.0% p-(5-pentyl-2-pyrimidinyl)benzonitrile,
11.0% p-(5-heptyl-2-pyrimidinyl)benzonitrile,
13.0% trans-4-propylcyclohexane carboxylic acid p-cyanophenyl ester,
11.0% trans-4-pentylcyclohexane carboxylic acid p-cyanophenyl ester,
20.0% trans-4-butylcyclohexane carboxylic acid p-(ethoxy)phenyl ester,
18.0% trans-4-pentylcyclohexane carboxylic acid p-(methoxy)phenyl ester,
b 7.0% 4''-pentyl-4-cyano-p-terphenyl, and
8.0% trans-p-[5-(4-pentylcyclohexyl)-2-pyrimidinyl]-benzonitrile, melting point <0° C.; clearing point 85° C.

Mixture 49:
17.5% 4'-Heptyl-4-cyanobiphenyl,
5.0% p-(5-pentyl-2-pyrimidinyl)benzonitrile,
9.0% p-(5-heptyl-2-pyrimidinyl)benzonitrile,
11.0% trans-4-propylcyclohexane carboxylic acid p-cyanophenyl ester, 6.0% trans-4-butylcyclohexane carboxylic acid p-cyanophenyl ester,
9.0% trans-4-pentylcyclohexane carboxylic acid p-cyanophenyl ester,
15.5% trans-4-pentylcyclohexane carboxylic acid p-(methoxy)phenyl ester,
17.0% trans-4-butylcyclohexane carboxylic acid p-(ethoxy)phenyl ester, and
10.0% trans-p-[5-(4-ethylcyclohexyl)-2-pyrimidinyl]benzonitrile, melting point <0° C.; clearing point 69° C.

Mixture 50:
23.0% 4'-Heptyl-4-cyanobiphenyl,
7.0% p-(5-pentyl-2-pyrimidinyl)benzonitrile,
12.0% p-(5-heptyl-2-pyrimidinyl)benzonitrile,
14.0% trans-4-propylcyclohexane carboxylic acid p-cyanophenyl ester,
12.0% trans-4-pentylcyclohexane carboxylic acid p-cyanophenyl ester,
20.0% trans-4-pentylcyclohexane carboxylic acid p-(methoxy)phenyl ester, and
12.0% trans-p-[5-(4-ethylcyclohexyl)-2-pyrimidinyl]benzonitrile, melting point <0° C.; clearing point 70° C.

Mixture 51:
6.0% p-Butylbenzoic acid p'-cyanophenyl ester,
7.0% p-(5-pentyl-2-pyrimidinyl)benzonitrile,
12.0% p-(5-heptyl-2-pyrimidinyl)benzonitrile,
14.0% trans-4-propylcyclohexane carboxylic acid p-cyanophenyl ester,
8.0% trans-4-butylcyclohexane carboxylic acid p-cyanophenyl ester,
12.0% trans-4-pentylcyclohexane carboxylic acid p-cyanophenyl ester,
22.0% trans-4-butylcyclohexane carboxylic acid p-(ethoxy)phenyl ester,
8.0% 4''-pentyl-4-cyano-p-terphenyl, and
11.0% trans-p-[5-(4-ethylcyclohexyl)-2-pyrimidinyl]benzonitrile, melting point <0° C.; clearing point 89° C.

Mixture 52:
18.0% 4'-Heptyl-4-cyanobiphenyl,
5.0% p-butylbenzoic acid p'-cyanophenyl ester,
5.0% p-(5-pentyl-2-pyrimidinyl)benzonitrile,
9.5% p-(5-heptyl-2-pyrimidinyl)benzonitrile;
11.0% trans-4-propylcyclohexane carboxylic acid p-cyanophenyl ester,
9.5% trans-4-pentylcyclohexane carboxylic acid p-cyanophenyl ester,
18.0% trans-4-butylcyclohexane carboxylic acid p-(ethoxy)phenyl ester,
10.0% trans-p-[5-(4-ethylcyclohexyl)-2-pyrimidinyl]benzonitrile, and
14.0% trans-p-[5-(4-heptylcyclohexyl)-2-pyrimidinyl]benzonitrile, melting point <0° C.; clearing point 93° C.

Mixture 53:
5.0% p-Butylbenzoic acid p'-cyanophenyl ester,
5.0% p-(5-pentyl-2-pyrimidinyl)benzonitrile,
10.0% p-(5-heptyl-2-pyrimidinyl)benzonitrile,
11.0% trans-4-propylcyclohexane carboxylic acid p-cyanophenyl ester,
10.0% trans-4-pentylcyclohexane carboxylic acid p-cyanophenyl ester,
18.0% trans-4-butylcyclohexane carboxylic acid p-(ethoxy)phenyl ester,
17.0% trans-4-pentylcyclohexane carboxylic acid p-(methoxy)phenyl ester,
10.0% trans-p-[5-(4-ethylcyclohexyl)-2-pyrimidinyl]benzonitrile, and
14.0% trans-p-[5-(4-heptylcyclohexyl)-2-pyrimidinyl]benzonitrile, melting point <0° C.; clearing point 98° C.

Mixture 54:
15.0% 4'-Heptyl-4-cyanobiphenyl,
4.0% p-butylbenzoic acid p'-cyanophenyl ester,
4.5% p-(5-pentyl-2-pyrimidinyl)benzonitrile,
8.0% p-(5-heptyl-2-pyrimidinyl)benzonitrile,
9.5% trans-4-propylcyclohexane carboxylic acid p-cyanophenyl ester,
8.0% trans-4-pentylcyclohexane carboxylic acid p-cyanophenyl ester,
15.0% trans-4-butylcyclohexane carboxylic acid p-(ethoxy)phenyl ester,
14.0% trans-4-pentylcyclohexane carboxylic acid p-(methoxy)phenyl ester,
9.0% trans-p-[5-(4-ethylcyclohexyl)-2-pyrimidinyl]benzonitrile, and
13.0% trans-p-[5-(4-heptylcyclohexyl)-2-pyrimidinyl]benzonitrile, melting point <0° C.; clearing point 92° C.

Mixture 55:
33.0% 4'-Pentyl-4-cyanobiphenyl,
8.5% trans-4-propylcyclohexane carboxylic acid p-cyanophenyl ester,
7.0% trans-4-pentylcyclohexane carboxylic acid p-cyanophenyl ester,
14.0% trans-4-butylcyclohexane carboxylic acid p-(ethoxy)phenyl ester,
12.5 o/o trans-4-pentylcyclohexane carboxylic acid p-(methoxy)phenyl ester,
8.0 o/o trans-p-[5-(4-ethylcyclohexyl)-2-pyrimidinyl]benzonitrile,
5.0 o/o trans-p-[5-(4-pentylcyclohexyl)-2-pyrimidinyl]benzonitrile, and
12.0 o/o trans-p-[5-(4-heptylcyclohexyl)-2-pyrimidinyl]benzonitrile, melting point <0° C.; clearing point 96° C.

Mixture 56:
45.0 o/o 4'-Pentyl-4-cyanobiphenyl,
6.0 o/o p-butylbenzoic acid p'-cyanophenyl ester,
6.0 o/o p-(5-pentyl-2-pyrimidinyl)benzonitrile,
13.0 o/o trans-4-propylcyclohexane carboxylic acid p-cyanophenyl ester,
7.5 o/o trans-4-butylcyclohexane carboxylic acid p-cyanophenyl ester,
11.5 o/o trans-4-pentylcyclohexane carboxylic acid p-cyanophenyl ester, and
11.0 o/o trans-p-[5-(4-ethylcyclohexyl)-2-pyrimidinyl]benzonitrile, melting point <0° C.; clearing point 65° C.

Mixture 57:
41.0 o/o 4'-Pentyl-4-cyanobiphenyl,
5.0 o/o p-Butylbenzoic acid p'-cyanophenyl ester,
5.0 o/o p-(5-pentyl-2-pyrimidinyl)benzonitrile,
12.0 o/o trans-4-propylcyclohexane carboxylic acid p-cyanophenyl ester,
10.0 o/o trans-4-pentylcyclohexane carboxylic acid p-cyanophenyl ester,
16.0 o/o trans-4-pentylcyclohexane carboxylic acid p-(methoxy)phenyl ester, and
11.0 o/o trans-p-[5-(4-ethylcyclohexyl)-2-pyrimidinyl]benzonitrile, melting point <0° C.; clearing point 65° C.

Mixture 58:
29.0 o/o 4'-Heptyl-4-cyanobiphenyl, 8.0 o/o p-butylbenzoic acid p'-cyanophenyl ester,
8.0 o/o p-(5-pentyl-2-pyrimidinyl)benzonitrile,
17.0 o/o trans-4-propylcyclohexane carboxylic acid p-cyanophenyl ester,
10.0 o/o trans-4-butylcyclohexane carboxylic acid p-cyanophenyl ester,
15.0 o/o trans-4-pentylcyclohexane carboxylic acid p-cyanophenyl ester, and
13.0 o/o trans-p-[5-(4-ethylcyclohexyl)-2-pyrimidinyl]benzonitrile, melting point <0° C.; clearing point 73° C.

Mixture 59:
21.0 o/o 4'-Heptyl-4-cyanobiphenyl,
5.0 o/o p-butylbenzoic acid p'-cyanophenyl ester,
6.0 o/o p-(5-pentyl-2-pyrimidinyl)benzonitrile,
11.0 o/o p-(5-heptyl-2-pyrimidinyl)benzonitrile,
13.0 o/o trans-4-propylcyclohexane carboxylic acid p-cyanophenyl ester,
11.0 o/o trans-4-pentylcyclohexane carboxylic acid p-cyanophenyl ester,
21.0 o/o trans-4-butylcyclohexane carboxylic acid p-(ethoxy)phenyl ester, and
12.0 o/o trans-p-[5-(4-ethylcyclohexyl)-2-pyrimidinyl]benzonitrile, melting point <0° C.; clearing point 71° C.

Mixture 60:
37.0 o/o 4'-Pentyl-4-cyanobiphenyl,
5.0 o/o p-(5-pentyl-2-pyrimidinyl)benzonitrile,
8.0 o/o p-(5-heptyl-2-pyrimidinyl)benzonitrile,
28.0 o/o trans-p-(4-pentylcyclohexyl)benzonitrile,
9.0 o/o trans-p-[5-(4-ethylcyclohexyl)-2-pyrimindyl]benzonitrile, and
13.0 o/o trans-p-[5-(4-heptylcyclohexyl)-2-pyrimidinyl]benzonitrile, melting point <0° C.; clearing point 84° C.

Mixture 61:
3.5 o/o p-Butylbenzoic acid p'-cyanophenyl ester,
4.0 o/o p-(5-pentyl-2-pyrimidinyl)benzonitrile,
7.0 o/o p-(5-heptyl-2-pyrimidinyl)benzonitrile,
25.0 o/o trans-p-(4-pentylcyclohexyl)benzonitrile,
8.5 o/o trans-4-propylcyclohexane carboxylic acid p-cyanophenyl ester,
7.0 o/o trans-4-pentylcyclohexane carboxylic acid p-cyanophenyl ester,
13.0 o/o trans-4-butylcyclohexane carboxylic acid p-(ethoxy)phenyl ester,
12.0 o/o trans-4-pentylcyclohexane carboxylic acid p-(methoxy)phenyl ester,
8.0 o/o trans-p-[5-(4-ethylcyclohexyl)-2-pyrimidinyl]benzonitrile, and
12.0 o/o trans-p-[5-(4-heptylcyclohexyl)-2pyrimidinyl]benzonitrile, melting point <0° C.; clearing point 89° C.

Mixture 62:
37.0 o/o 4'-Pentyl-4-cyanobiphenyl,
21.0 o/o 4'-pentyloxy-4-cyanobiphenyl,
4.0 o/o p-butylbenzoic acid p'-cyanophenyl ester,
5.0 o/o p(5-pentyl-2-pyrimidinyl)benzonitrile,
8.0 o/o p-(5-heptyl-2-pyrimidinyl)benzonitrile,
15.0 o/o trans-4-butylcyclohexane carboxylic acid p-(ethoxy)phenyl ester, and
10.0 o/o trans-p-[5-(4-ethylcyclohexyl)-2-pyrimidinyl]benzonitrile, melting point <0° C.; clearing point 65° C.

Mixture 63:
43.0 o/o 4'-Pentyl-4-cyanobiphenyl,
24.0 o/o 4'-Pentyloxy-4-cyanobiphenyl,
6.0 o/o p-(5-pentyl-2-pyrimidinyl)benzonitrile,
11.0 o/o p-(5-heptyl-2-pyrimidinyl)benzonitrile,
10.0 o/o trans-p-[5-(4-ethylcyclohexyl)-2-pyrimidinyl]benzonitrile, and
6.0 o/o trans-p-[5-(4-butylcyclohexyl)-2-pyrimidinyl]benzonitrile, melting point <0° C.; clearing point 70° C.

Mixture 64:
44.0 o/o 4'-Pentyl-4-cyanobiphenyl,
21.0 o/o 4'-heptyl-4-cyanobiphenyl,
6.0 o/o p-(5-pentyl-2-pyrimidinyl)benzonitrile,
12.0 o/o p-(5-heptyl-2-pyrimidinyl)benzonitrile,
11.0 o/o trans-p-[5-(4-ethylcyclohexyl)-2-pyrimidinyl]benzonitrile, and
6.0 o/o trans-p-[5-(4-butylcyclohexyl)-2-pyrimidinyl]benzonitrile, melting point <0° C.; clearing point 70° C.

Mixture 65:
41.0 o/o 4'-Pentyl-4-cyanobiphenyl,
19.0 o/o 4'-heptyl-4-cyanobiphenyl,
5.0 o/o p-(5-pentyl-2-pyrimidinyl)benzonitrile,
10.0 o/o p-(5-heptyl-2-pyrimidinyl)benzonitrile,
18.0 o/o trans-4-butylcyclohexane carboxylic acid p-(ethoxy)phenyl ester, and
7.0 o/o trans-p-[5-(4-pentylcyclohexyl)-2-pyrimidinyl]benzonitrile, melting point <0° C.; clearing point 58° C.

Mixture 66:
47.0 o/o 4'-Pentyl-4-cyanobiphenyl,
23.0 o/o 4'-heptyl-4-cyanobiphenyl,
7.0 o/o p-(5-pentyl-2-pyrimidinyl)benzonitrile,
11.0 o/o p-(5-heptyl-2-pyrimidinyl)benzonitrile, and
12.0 o/o trans-p-[5-(4-ethylcyclohexyl)-2-pyrimidinyl]benzonitrile, melting point <0° C.; clearing point 60° C.

Mixture 67:
36.0 o/o 4'-Pentyl-4-cyanobiphenyl,
15.0 o/o 4'-heptyl-4-cyanobiphenyl,
5.0 o/o p-(5-pentyl-2-pyrimidinyl)benzonitrile,
8.0 o/o p-(5-heptyl-2-pyrimidinyl)benzonitrile,
15.0 o/o trans-4-butylcyclohexane carboxylic acid p-(ethoxy)phenyl ester,
14.0 o/o trans-4-pentylcyclohexane carboxylic acid p-(methoxy)phenyl ester, and
7.0 o/o trans-p-[5-(4-pentylcyclohexyl)-2-pyrimidinyl]benzonitrile, melting point <0° C.; clearing point 59° C.

Mixture 68:
55.0 o/o 4'-Pentyl-4-cyanobiphenyl,
11.0 o/o 4'-octyloxy-4-cyanobiphenyl,
9.0 o/o p-(5-pentyl-2-pyrimidinyl)benzonitrile,
16.0 o/o p-(5-heptyl-2-pyrimidinyl)benzonitrile, and
9.0 trans-p-[5-(4-pentylcyclohexyl)-2-pyrimidinyl]benzonitrile, melting point <0° C.; clearing point 65° C.

Mixture 69:
40.0 o/o 4'-Pentyl-4-cyanobiphenyl,
23.0 o/o 4'-pentyloxy-4-cyanobiphenyl,
5.0 o/o p-(5-pentyl-2-pyrimidinyl)benzonitrile,
10.0 o/o p-(5-heptyl-2-pyrimidinyl)benzonitrile,
16.0 o/o trans-4-pentylcyclohexane carboxylic acid p-(methoxy)phenyl ester, and
6.0 o/o trans-p-[5-(4-pentylcyclohexyl)-2-pyrimidinyl]benzonitrile, melting point <0° C.; clearing point 62° C.

Mixture 70:
7.0 o/o 4'-Pentyl-4-cyanobiphenyl,
5.6 o/o p-butylbenzoic acid p'-cyanophenyl ester,
6.5 o/o p-(5-pentyl-2-pyrimidinyl)benzonitrile, 12.1 o/o p-(5-heptyl-2-pyrimidinyl)benzonitrile,
7.4 o/o trans-4-butylcyclohexane carboxylic acid p-cyanophenyl ester,
11.2 o/o trans-4-pentylcyclohexane carboxylic acid p-cyanophenyl ester,
20.4 o/o trans-4-butylcyclohexane carboxylic acid p-(ethoxy)phenyl ester,
18.6 o/o trans-4-pentylcyclohexane carboxylic acid p-(methoxy)phenyl ester, and
11.2 o/o trans-p-[5-(4-ethylcyclohexyl)-2-pyrimidinyl]benzonitrile, melting point <0° C.; clearing point 71° C.

Mixture 71:
31.0 o/o 4'-Pentyl-4-cyanobiphenyl,
30.0 o/o p-[(p-hexylbenzyliden)amino]benzonitrile,
12.0 o/o trans-4-butylcyclohexane carboxylic acid p-(ethoxy)phenyl ester,
19.0 o/o trans-4-pentylcyclohexane carboxylic acid p-(propyloxy)phenyl ester, and
8.0 o/o trans-p-[5-(4-ethylcyclohexyl)-2-pyrimidinyl]benzonitrile, melting point <0° C.; clearing point 66° C.

Mixture 72:
5.0 o/o p-Butylbenzoic acid p'-cyanophenyl ester
4.0 o/o p-pentylbenzoic acid p'-cyanophenyl ester
26.0 o/o p-[(p-butylbenzyliden)amino]benzonitrile,
5.0 o/o p-(5-pentyl-2-pyrimidinyl)benzonitrile,
10.0 o/o p-(5-heptyl-2-pyrimidinyl)benzonitrile,
11.0 o/o trans-4-propylcyclohexane carboxylic acid p-cyanophenyl ester,
10.0 o/o trans-4-pentylcyclohexane carboxylic acid p-cyanophenyl ester,
19.0 o/o trans-4-butylcyclohexane carboxylic acid p-(ethoxy)phenyl ester, and
10.0 o/o trans-p-[5-(4-ethylcyclohexyl)-2-pyrimidinyl]benzonitrile, melting point <0° C.; clearing point 73° C.

Mixture 73:
6.0 o/o 4'-Octyloxy-4-cyanobiphenyl,
7.0 o/o p-butylbenzoic acid p'-cyanophenyl ester,
6.0 o/o p-(5-pentyl-2-pyrimidinyl)benzonitrile,
12.0 o/o p-(5-heptyl-2-pyrimidinyl)benzonitrile,
12.0 o/o trans-4-propylcyclohexane carboxylic acid p-cyanophenyl ester,
11.0 o/o trans-4-pentylcyclohexane carboxylic acid p-cyanophenyl ester,
19.0 o/o trans-4-butylcyclohexane carboxylic acid p-(ethoxy)phenyl ester,
18.0 o/o trans-4-pentylcyclohexane carboxylic acid p-(methoxy)phenyl ester, and
9.0 o/o trans-p-[5-(4-ethylcyclohexyl)-2-pyrimidinyl]benzonitrile, melting point <0° C.; clearing point 71° C.

Mixture 74:
23.0 o/o 4'-Heptyl-4-cyanobiphenyl,
21.0 o/o trans-4-butylcyclohexane carboxylic acid p-(ethoxy)phenyl ester,
19.0 o/o trans-4-pentylcyclohexane carboxylic acid p-(methoxy)phenyl ester,
26.0 o/o trans-4-pentylcyclohexane carboxylic acid p-(propyloxy)phenyl ester, and
11.0 o/o trans-p-[5-(4-ethylcyclohexyl)-2-pyrimidinyl]benzonitrile, melting point <0° C.; clearing point 73° C.

Mixture 75:
75.0 wt. % mixture 74 and
25.0 wt. % mixture 47, melting point <0° C.; clearing point 71.9° C.

Mixture 76:
60.0 wt. % mixture 74 and
40.0 wt. % mixture 47, melting point <0° C.; clearing point 71.7° C.

Mixture 77:
45.0 wt. % mixture 74 and
55.0 wt. % mixture 47, melting point <0° C.; clearing point 71.8° C.

Mixture 78:
15.0 wt. % mixture 74 and
85.0 wt. % mixture 47, melting point <0° C.; clearing point 72.4° C.

Mixture 79:
75.0 wt. % mixture 74 and
25.0 wt. % mixture 70, melting point <0° C.; clearing point 71.5° C.

Mixture 80:
15.0 wt. % mixture 74 and
85.0 wt. % mixture 70, melting point <0° C.; clearing point 70.6° C.

Mixture 81:
22.0 o/o 4'-Heptyl-4-cyanobiphenyl,
13.0 o/o trans-4-propylcyclohexane carboxylic acid p-cyanophenyl ester,
21.0 o/o trans-4-butylcyclohexane carboxylic acid p-(ethoxy)phenyl ester,
19.0 o/o trans-4-pentylcyclohexane carboxylic acid p-(methoxy)phenyl ester,
18.0 o/o trans-4-pentylcyclohexane carboxylic acid p-(propyloxy)phenyl ester, and
7.0 o/o trans-p-[5-(4-pentylcyclohexyl)-2-pyrimidinyl]benzonitrile, melting point <0° C.; clearing point 71.6° C.

Mixture 82:
Mixture 55+colouring substance of formula IXa in which $R^8$ represents a n-heptyl group; melting point <0° C.; clearing point 97° C.; blue; $\lambda_{max}$=594 nm; S=0.745.

Mixture 83:
Mixture 46+colouring substance of formula IXa in which $R^8$ represents a n-heptyl group; melting point <0° C.; clearing point 96° C.; blue; $\lambda_{max}$=594 nm; S=0.707.

Mixture 84:
Mixture 47+colouring substance of formula IXa in which $R^8$ represents a n-heptyl group; melting point <0° C.; clearing point 73° C.; blue; $\lambda_{max}$=594 nm; S=0.717.

Mixture 85:
Mixture 53+colouring substance of formula IXa in which $R^8$ represents a n-butyl group; melting point <0° C.; clearing point 98° C.; blue; $\lambda_{max}$=594 nm; S=0.709.

Mixture 86:
Mixture 53+colouring substance of formula IXa in which $R^8$ represents a methyl group; melting point <0° C.; clearing point 98° C.; blue; $\lambda_{max}$=594 nm; S=0.694.

Mixture 87:
Mixture 31+colouring substance of formula IXa in which $R^8$ represents a n-heptyl group; melting point <0° C.; clearing point 102° C.; blue; $\lambda_{max}$=594 nm; S=0.768.

Mixture 88:
Mixture 46+colouring substance of formula VIIa in which $R^7$ represents a n-butyloxy group, $Z^3$ represents a dimethylamino group and $n_4$ stands for zero; melting point <0° C.; clearing point 97° C.; red; $\lambda_{max}$=509 nm; S=0.683.

Mixture 89:

Mixture 55+colouring substance of formula VIIa in which $X^7$ represents an ethoxy group, $Z^3$ represents a dimethylamino group and $n_4$ stands for zero; melting point <0° C.; clearing point 97° C.; red; $\lambda_{max}=514$ nm.

Mixture 90:

Mixture 55+colouring substance of formula XI in which $R^4$ represents an ethyl group; melting point <0° C.; clearing point 97° C.; yellow; $\lambda_{max}=446$ nm; $S=0.889$.

Mixture 91:

Mixture 55+colouring substance of formula IVa; melting point −0° C.; clearing point 97° C.; yellow-red; $\lambda_{max}=500$ nm; $S=0.817$.

Mixture 92:

Mixture 55+colouring substance of formula VIIa in which $R^7$ represents a nitro group, $Z^3$ represents a diethylamino group and $n_4$ stands for 1; melting point <0° C.; clearing point 97° C.; steel blue; $\lambda_{max}=605$ nm; $S=0.816$.

Mixture 93:

Mixture 55+colouring substance of formula XII in which $R^5$ represents an ethyl group; melting point <0° C.; clearing point 97° C.; blue; $\lambda_{max}=636$ nm; $S=0.716$.

Mixture 94:

35.0 o/o 4′-Pentyl-4-cyanobiphenyl,
4.0 o/o p-butylbenzoic acid p′-cyanophenyl ester,
4.0 o/o p-pentylbenzoic acid p′-cyanophenyl ester,
4.0 o/o p-(5-pentyl-2-pyrimidinyl)benzonitrile,
8.0 o/o p-(5-heptyl-2-pyrimidinyl)benzonitrile,
9.0 o/o trans-4-propylcyclohexane carboxylic acid p-cyanophenyl ester,
8.0 o/o trans-4-pentylcyclohexane carboxylic acid p-cyanophenyl ester,
19.0 o/o trans-4-pentylcyclohexane carboxylic acid p-(propyloxy)phenyl ester, and
9.0 o/o trans-p-[5-(4-ethylcyclohexyl)-2-pyrimidinyl]benzonitrile, melting point <0° C.; clearing point 63° C.

Mixture 95:

33.0 o/o 4′-Pentyl-4-cyanobiphenyl,
30.0 o/o 4′-hexyl-4-cyanobiphenyl,
5.0 o/ 4′-octyloxy-4-cyanobiphenyl,
4.0 o/o p-(5-pentyl-2-pyrimidinyl)benzonitrile,
8.0 o/o p-(5-heptyl-2-pyrimidinyl)benzonitrile,
3.0 o/o p-butylbenzoic acid p′-cyanophenyl ester,
7.0 o/o trans-4-pentylcyclohexane carboxylic acid p-cyanophenyl ester, and
10.0 o/o trans-p-[5-(4-ethylcyclohexyl)-2-pyrimidinyl]benzonitrile, melting point <0° C.; clearing point 58° C.

Mixture 96:

25.5 o/o 4′-Heptyl-4-cyanobiphenyl,
13.0 o/o p-[(p-propylbenzyliden)amino]benzonitrile,
7.0 o/o p-butylbenzoic acid p′-cyanophenyl ester,
6.0 o/o p-pentylbenzoic acid p′-cyanophenyl ester,
7.5 o/o p-(5-pentyl-2-pyrimidinyl)benzonitrile,
14.0 o/o p-(5-heptyl-2-pyrimidinyl)benzonitrile,
15.0 o/o trans-4-propylcyclohexane carboxyic acid p-cyanophenyl ester, and
12.0 o/o trans-p-[5-(4-ethylcyclohexyl)-2-pyrimidinyl]benzonitrile, melting point <0° C.; clearing point 70° C.

For mixtures which contain coloring substances there also come into consideration other liquid crystal matrices insofar as the clearing points are higher than about 80° C. Preferred liquid crystal matrices for mixtures which contain coloring substances are mixtures 2, 15, 24, 25, 27, 31, 39–42, 46–48, 52–55 and 61 hereinbefore.

The following Examples illustrate the process provided by the present invention:

EXAMPLE 1

Preparation of trans-p-[5-(4-n-pentylcycohexyl)-2-pyrimidinyl]benzonitrile 9.5 Ml. of benzenesulfonyl chloride are added dropwise while stirring to a suspension of 17.2 g. of crude trans-p-[5-(4-n-pentylcyclohexyl)-2-pyrimidinyl]benzamide in 150 ml. of pyridine. The mixture is then warmed to 55° C. for 6 hours in an oil-bath. The mixture is poured into 500 ml. of ice-cold 0.5-N hydrochloric acid and the product is taken up in methylene chloride. The extract is washed three times with 200 ml. of 3-N hydrochloric acid each time, then with 100 ml. of saturated sodium bicarbonate solution and with water, dried over sodium sulfate and evaporated. The crude product is chromatographed on a column of 600 g. of silica gel with toluene/5% acetone (v/v). The fractions which are pure according to thin-layer chromatography are dissolved in hexane, filtered hot with active carbon and recrystallized. There is obtained trans-p-[5-(4-n-pentylcyclohexyl)-2-pyrimidinyl]benzonitrile; melting point 100.5° C., clearing point 231° C.

The trans-p-[5-(4-n-pentylcyclohexyl)-2-pyrimidinyl]-benzamide used as the starting material can be prepared as follows:

(a) A solution of 63.9 g. of trans-4-n-pentylcyclohexane carboxylic acid in 250 ml. of dry ether is added dropwise to a suspension of 12.2 g. of lithium aluminum hydride in 1000 ml. of dry ether in such a manner that the mixture boils slightly. After completion of the dropwise addition, the mixture is stirred for a further 1 hour. There are then cautiously added dropwise 80 ml. of ethyl acetate and thereafter 100 ml. of ice-water. The reaction mixture is poured into ice-water and made Congo acid with dilute hydrochloric acid. The organic phase is separated, washed in sequence with water, sodium bicarbonate solution and water, dried over sodium sulfate and evaporated. The resulting trans-4-n-pentylcyclohexane carbinol is used in the next step without purification.

(b) A solution of 59.0 g. of trans-4-n-pentylcyclohexane carbinol in 100 ml. of ether is added to a suspension of 125 g. of pyridinium chlorochromate in 900 ml. of methylene chloride and the mixture is stirred at room temperature for 2 hours. The mixture is then diluted with 400 ml. of ether, stirred for a further 15 minutes and the solution is decanted off from the tarry precipitate. The precipitate is back-washed with ether. The combined organic solutions are filtered through a Florisil column. The trans-4-n-pentylcyclohexane carboxaldehyde obtained after evaporation of the filtrate is used directly in the next step.

(c) A suspension of 223.1 g. of (methoxymethyl)triphenylphosphonium chloride in 1600 ml. of dry ether is treated with 76.2 g. of potassium tert.butylate. After stirring for 45 minutes, a solution of 51.4 g. of trans-4-n-pentylcyclohexane carboxaldehyde in 300 ml. of ether is added dropwise. The mixture is stirred for a further 2 hours and then poured into 2.5 liters of ice-water. The organic phase is separated, washed neutral with water, dried over sodium sulfate and evaporated. The resulting crude trans-2-(4-n-pentylcyclohexyl)vinyl methyl ether is distilled at 92°–96°

C./0.7 mmHg in order to separate the residual triphenylphosphine.

(d) 38.7 g. of trans-2-(4-n-pentylcyclohexyl)vinyl methyl ether are added dropwise while stirring to a solution, cooled to 0° C., of 13.1 g. of boron trifluoride diethyl etherate in 700 ml. of freshly distilled triethyl orthoformate and the mixture is stirred at room temperature overnight. The mixture is then diluted with 1000 ml. of toluene, washed with 200 ml. of sodium bicarbonate solution and then with water, dried over sodium sulfate, filtered and evaporated. The crude trans-(4-n-pentylcyclohexyl)malonic bisacetal is used in the next step without further purification.

(e) 57.4 g. of crude trans-(4-n-pentylcyclohexyl)malonic bis-acetal are treated with 3.5 ml. of water and 150 mg. of p-toluenesulfonic acid. The mixture is stirred at 80°-85° C. for 3 hours. The mixture is then left to cool, 1.6 g. of sodium bicarbonate are added and the resulting mixture is stirred at room temperature for 1.5 hours. The mixture is diluted with ether, washed with three 50 ml. portions of ice-cold 3-N sodium hydroxide, washed neutral with water, dried over sodium sulfate, filtered and evaporated. The crude 3-ethoxy-2-(trans-4-n-pentylcyclohexyl)acrolein is used immediately in the next step.

(f) A sodium methylate solution is prepared by the cautious addition of 4.8 g. of sodium in small portions to 175 ml. of absolute methanol. 17.8 g. of 3-ethoxy-2-(trans-4-n-pentylcyclohexyl)acrolein are added dropwise to the sodium methylate solution while stirring, the mixture is stirred for a further 10 minutes and then 16.2 g. of p-carbamoylbenzamide hydrochloride are added thereto. The mixture is stirred at 50° C. overnight. After cooling, the mixture is acidified with 55 ml. of 3-N hydrochloric acid. The suspension is filtered under suction, the residue is washed neutral on the filter with water, sucked dry and dried at 70° C. in a water-jet vacuum. The brownish crude trans-p-[5-(4-n-pentyl-cyclohexyl)-2-pyrimidinyl]benzamidine is used in the process described in the first paragraph of this Example without purification.

The following pyrimidine derivatives of formula I can be manufactured in an analogous manner:

Trans-p-[5-(4-methylcyclohexyl)-2-pyrimidinyl]benzonitrile; melting point 150.5° C., clearing point 213.5° C.;

trans-p-[5-(4-ethylcylohexyl)-2-pyrimidinyl]benzonitrile; melting point 118° C., clearing point 225° C.;

trans-p-[5-(4-n-propylcyclohexyl)-2-pyrimidinyl]benzonitrile; melting point 122.5° C., clearing point 243.5° C.;

trans-p-[5-(4-n-butylcyclohexyl)-2-pyrimidinyl]benzonitrile; melting point 118° C., clearing point 234° C.;

trans-p-[5-(4-n-hexylcyclohexyl)-2-pyrimidinyl]benzonitrile; melting point 91.5° C., clearing point 224.5° C.;

trans-p-[5-(4-n-heptylcyclohexyl)-2-pyrimidinyl]benzonitrile; melting point 80.5° C., clearing point 219° C.;

(+)-trans-p-{5-[4-(2-methylbutyl)cyclohexyl]-2-pyrimidinyl}benzonitrile; $\alpha_D = +9$, melting point 76°, smectic-cholesteric phase transition 125° C., clearing point 178° C.; and (+)-trans-p-{5-[4-(3-methylpentyl)cyclohexyl]-2-pyrimidinyl}benzonitrile; $\alpha_D = +7$, melting point 101° C., smectic-cholesteric phase transition 159° C., clearing point 189.5° C.

EXAMPLE 2

Preparation of trans-4-[5-(p-n-heptylphenyl)-2-pyrimidinyl]cyclohexane carbonitrile 6.0 Ml. of benzenesulfonyl chloride are added dropwise while stirring to a suspension of 10.8 g. of trans-4-[5-(p-n-heptylphenyl)-2-pyrimidinyl]cyclohexane carboxamide in 150 ml. of pyridine. The mixture is then warmed to 55° C. for 2 hours in an oilbath. The mixture is poured into ice-water and the product is taken up in methylene chloride. The extract is washed successively with dilute hydrochloric acid, saturated sodium bicarbonate solution and water, dried over sodium sulfate and evaporated. The crude product is chromatographed on a column of 300 g. of silica gel with toluene/5% acetone (v/v). The fractions which are pure according to thin-layer chromatography are combined and evaporated. The residue is dissolved in hexane, filtered hot with active carbon and recrystallized. The crystallizate is dried in vacuo overnight. There is obtained trans-4-[5-(p-n-heptylphenyl)-2-pyrimidinyl]cyclohexane carbonitrile; melting point 83.5° C., clearing point 160° C.

The trans-4-[5-(p-n-heptylphenyl)-2-pyrimidinyl]cyclohexane carboxamide used as the starting material can be prepared as follows:

(a) 96.6 g. of trans-4-cyanocyclohexane carboxylic acid methyl ester are dissolved under an inert gas in 130 ml. of absolute methanol and 150 ml. of dry benzene. Dry hydrogen chloride is conducted in at 0° C. while stirring until the solution is saturated. The colorless solution is stirred overnight, whereby the product, trans-4-carbomethoxycyclohexane-carbimidic acid methyl ester hydrochloride, begins to crystallize out. The mixture is left to stand for a further three days and then the precipitated iminoester hydrochloride is removed by filtration. 100.7 G. of the precipitated crude product suspended in 150 ml. of methanol are, after cooling to about −40° C., treated with 70 g. of liquid ammonia and shaken at +70° C. for 24 hours in an autoclave. After cooling the reaction mixture to room temperature and discharging the excess ammonia, the suspension is evaporated, the solid product is washed several times on the filter with ether and the residue remaining behind is recrystallized from methanol to give trans-4-carbamoylcyclohexane-carboxamidine hydrochloride.

(b) To a sodium methylate solution prepared by the addition of 3.2 g. of sodium to 125 ml. of methanol are added 12.6 g. of 3-ethoxy-2-(p-n-heptylphenyl)acrolein and then 9.9 g. of trans-4-carbamoylcyclohexane-carboxamidine hydrochloride. The mixture is stirred at 50° C. overnight. The mixture is then acidified with dilute hydrochloric acid and the suspension is filtered. The residue is washed neutral and dried in vacuo. For purification, the residue is boiled with ether. There is obtained trans-4-[5-(p-n-heptylphenyl)-2-pyrimidinyl]cyclohexane carboxamide which is difficultly soluble.

The following pyrimidine derivatives of formula I can be manufactured in an analogous manner:

Trans-4-[5-(p-methylphenyl)-2-pyrimidinyl]cyclohexane carbonitrile;

trans-4-[5-(p-ethylphenyl)-2-pyrimidinyl]cyclohexane carbonitrile; melting point 172° C., clearing point 197.5° C.;

trans-4-[5-(p-propylphenyl)-2-pyrimidinyl]cyclohexane carbonitrile; melting point 146° C., clearing point 194.5° C.;

trans-4-[5-(p-butylphenyl)-2-pyrimidinyl]cyclohexane carbonitrile; melting point 139.5° C., clearing point 179.5° C.;

trans-4-[5-(p-pentylphenyl)-2-pyrimidinyl]cyclohexane carbonitrile; melting point 112° C.; clearing point 175.5° C.;

trans-4-[5-(p-hexylphenyl)-2-pyrimidinyl]cyclohexane carbonitrile; melting point 84° C.; clearing point 163° C.; and trans-4-[5-(p-octylphenyl)-2-pyrimidinyl]cyclohexane carbonitrile; melting point 82.5° C.; clearing point 152.5° C.

EXAMPLE 3

Preparation of pure trans-4-[5-(trans-4-n-pentylcyclohexyl)-2-pyrimidinyl]-cyclohexane carbonitrile 7.2 Ml. of benzenesulfonyl chloride are added dropwise while stirring to a suspension of 13.2 g. of crude trans-4-[5-(trans-4-n-pentylcyclohexyl)-2-pyrimidinyl]-cyclohexane carboxamide in 150 ml. of pyridine. The mixture is then warmed to 55° C. for 3 hours in an oil-bath. The mixture is poured into 500 ml. of ice-water and the product is taken up in methylene chloride. The extract is washed successively with 3-N hydrochloric acid, saturated sodium bicarbonate solution and water, dried over sodium sulfate and evaporated. The crude product is chromatographed on a column of 500 g. of silica gel with toluene/5% acetate (v/v). The first fractions are mixtures and are discarded. The later fractions, which are uniform according to thin-layer chromatography, are dissolved in hexane, filtered hot with active carbon and recrystallized from the filtrate. There is obtained pure trans-4-[5-(trans-4-n-pentylcyclohexyl)-2-pyrimidinyl]cyclohexane carbonitrile; melting point 109.5° C., clearing point 175° C.

The trans-4-[5-(trans-4-n-pentylcyclohexyl)-2-pyrimidinyl]cyclohexane carboxamide used as the starting material can be prepared as follows:

16.0 g. of 3-ethoxy-2-(trans-4-n-pentylcyclohexyl)a-crolein (prepared as described in Example 1) are added dropwise while stirring to a sodium methylate solution prepared by the addition of 4.4 g. of sodium to 175 ml. of methanol and then 15.0 g. of trans-4-carbamoylcyclohexane carboxamidine hydrochloride (prepared as described in Example 2) are added thereto. The mixture is stirred at 50° C. overnight. The mixture is then acidified with dilute hydrochloric acid. The suspension is filtered. The residue is washed neutral with water and dried in vacuo. The resulting crude trans-4-[5-(trans-4-n-pentylcyclohexyl)-2-pyrimidinyl]cyclohexane carboxamide is used directly in the process described in the first paragraph of this Example.

The following pyrimidine derivatives of formula I can be manufactured in an analogous manner:

Trans-4-[5-(trans-4-methylcyclohexyl)-2-pyrimidinyl]-cyclohexane carbonitrile;

trans-4-[5-(trans-4-ethylcyclohexyl)-2-pyrimidinyl]-cyclohexane carbonitrile; melting point 166.5° C., clearing point 161° C.;

trans-4-[5-(trans-4-propylcyclohexyl)-2-pyrimidinyl]-cyclohexane carbonitrile; melting point 132° C., clearing point 184° C.;

trans-4-[5-(trans-4-butylcyclohexyl)-2-pyrimidinyl]-cyclohexane carbonitrile; melting point 121° C., clearing point 172° C.;

trans-4-[5-(trans-4-hexylcyclohexyl)-2-pyrimidinyl]-cyclohexane carbonitrile;

trans-4-[5-(trans-4-heptylcyclohexyl)-2-pyrimidinyl]-cyclohexane carbonitrile; melting point 102.5° C., clearing point 163.5° C.;

(+)-trans-4-{5-[trans-4-(2-methylbutyl)cyclohexyl]-2-pyrimidinyl}-cyclohexane carbonitrile; $\alpha_D = +10$; melting point 124° C., clearing point 125° C.; and (+)-trans-4-{5-[trans-4-(3-methylpentyl)cyclohexyl]-2-pyrimidinyl}cyclohexane carbonitrile; $\alpha_D = +7$; melting point 138° C., clearing point 134° C.

EXAMPLE 4

Preparation of trans-p-[5-(4-n-propyloxycyclohexyl)-2-pyrimidinyl]-benzonitrile 9.2 Ml. of benzenesulfonyl chloride are added dropwise while stirring to a suspension of 16.0 g. of trans-p-[5-(4-n-propyloxycyclohexyl)-2-pyrimidinyl]benzamide in 170 ml. of pyridine. The mixture is then warmed to 40° C. for 15 hours in an oil-bath. The clear mixture is poured into a mixture of 200 g. of ice and 24.1 ml. of concentrated hydrochloric acid and the product is taken up in methylene chloride. The extract is washed three times with 195 ml. of 3-N hydrochloric acid each time, then with 100 ml. of saturated sodium bicarbonate solution and with water, dried over sodium sulfate and evaporated. The crude product is chromatographed on a column of 200 g. of silica gel with benzene and with benzene containing 1% and 2% acetone (v/v). The fractions which are pure according to thin-layer chromatography are recrystallized from acetone/hexane. There is obtained trans-p-[5-(4-n-propyloxycyclohexyl)-2-pyrimidinyl]benzonitrile; melting point 114.5° C., clearing point 223.5° C.

The trans-p-[5-(4-n-propyloxy-cyclohexyl)-2-pyrimidinyl]benzamide used as the starting material can be prepared as follows:

(a) A solution of 41.0 g. of trans-4-n-propyloxycyclohexane carboxylic acid in 90 ml. of dry ether is added dropwise to a suspension of 8.4 g. of lithium aluminum hydride in 390 ml. of dry ether so that the mixture boils slightly. After completion of the dropwise addition, the mixture is stirred for a further 1 hour. There are then cautiously added dropwise 22 ml. of acetone and thereafter 35 ml. of water. The mixture is poured into ice-water and made Congo acid with 280 ml. of 3-N hydrochloric acid. The organic phase is separated, washed in sequence with water, sodium hydrogen carbonate solution and water, dried over sodium sulfate and evaporated. The trans-4-n-propyloxycyclohexane carbinol obtained is used in the next step without purification.

(b) A solution of 38.6 g. of trans-4-n-propyloxycyclohexane carbinol in 70 ml. of methylene chloride is added to a suspension of 85.9 g. of pyridinium chlorochromate in 620 ml. of methylene chloride and the mixture is stirred at room temperature for 2.5 hours. The mixture is then diluted with 275 ml. of ether, stirred for a further 15 minutes and the solution is decanted off from tarry precipitate. The precipitate is back-washed with ether. The combined organic solutions are filtered through a column of 175 g. of Florisil. The trans-4-n-propyloxycyclohexane carboxaldehyde obtained after evaporation of the filtrate is used directly in the next step.

(c) A suspension of 94.6 g. of (methoxymethyl)(triphenylphosphonium chloride in 1000 ml. of dry ether is treated with 33.0 g. of potassium tert.butylate. After stirring for 45 minutes, a solution of 31.4 g. of trans-4-n-propyloxycyclohexane carboxaldehyde in 200 ml. of ether is added dropwise. The mixture is stirred for a further 2.5 hours and then poured into 1.2 liters of ice-water. The organic phase is separated, washed neutral with water, dried over sodium sulfate and evaporated. The crude trans-2-(4-n-propyloxycyclohexyl)vinyl methyl ether obtained is distilled at 82°–85° C./0.6 mmHg in order to separate the residual triphenylphosphine.

(d) 28.0 g. of trans-2-(4-n-propyloxycyclohexyl)vinyl methyl ether are added dropwise while stirring to a solution, cooled to 0° C., 8.9 ml. of boron trifluoride diethyl etherate in 535 ml. of freshly distilled triethyl orthoformate and the mixture is stirred at room temperature overnight. The mixture is then diluted with 735 ml. of toluene, washed with 155 ml. of sodium bicarbonate solution and then with water, dried over sodium sulfate, filtered and evaporated. The crude trans-(4-n-propyloxycyclohexyl)malonic bis-acetal is used in the next step without further purification.

(e) 49.0 g. of crude trans-(4-n-propyloxycyclohexyl)malonic bis-acetal are treated with 3.1 ml. of water and 132 mg. of p-toluenesulfonic acid. The mixture is stirred at 85° C. for 2 hours. The mixture is then left to cool, 1.4 g. of sodium hydrogen carbonate are added and the resulting mixture is stirred at room temperature for 1.5 hours. The mixture is diluted with ether, washed with three 44 ml. portions of ice-cold 3-N sodium hydroxide each time and then with water, dried over sodium sulfate, filtered and evaporated. The crude 3-ethoxy-2-(trans-4-n-propyloxycyclohexyl)acrolein is used immediately in the next step.

(f) A sodium methylate solution is prepared from 9.7 g. of sodium and 392 ml. of absolute methanol. At room temperature there are added while stirring 31.4 g. of p-carbamoyl-benzamidine hydrochloride and then 29.8 g. of 3-ethoxy-2-(trans-4-n-propyloxycyclohexyl)acrolein dissolved in 100 ml. of absolute methanol. The mixture is stirred at 50° C. overnight while gassing with nitrogen, the yellow suspension is left to cool to room temperature and is then acidified with 131 ml. of 3-N hydrochloric acid. The suspension is filtered under suction and the precipitate is washed neutral with water and dried. For purification, the yellowish crude trans-p-[5-(4-n-propyloxycyclohexyl)-2-pyrimidinyl]benzamide is recrystallized from dioxan; melting point 261°–264° C. (decomposition).

The following pyrimidine derivatives of formula I can be manufactured in an analogous manner:

Trans-p-[5-(4-ethoxycyclohexyl)-2-pyrimidinyl]benzonitrile; melting point 144.5° C., clearing point 232° C.; and trans-p-[5-(4-pentyloxycyclohexyl)-2-pyrimidinyl]benzonitrile; melting point 93° C., clearing point 205° C.

We claim:

1. A compound of the formula

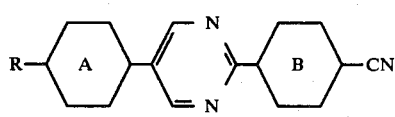

wherein at least one of the rings A and B is a trans-1,4-disubstituted cyclohexane ring and the other optionally is aromatic and R is straight-chain alkyl or alkoxy of 1 to 10 carbon atoms or a branched-chain alkyl of the formula $C_2H_5—(CH(CH_3))—(CH_2)_n$—wherein n is 1, 2 or 3.

2. In accordance with claim 1, a trans-p-[5-(4-alkyl- or 4-n-alkoxycyclohexyl)-2-pyrimidinyl]benzonitrile of the formula

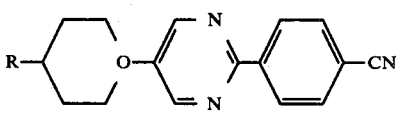

wherein R is straight-chain alkyl of 2 to 8 carbon atoms, straight-chain alkoxy of up to 6 carbon atoms or a branched-chain alkyl of the formula $C_2H_5—CH(CH_3)—(CH_2)_n$—wherein n is 1, 2 or 3.

3. In accordance with claim 1, a trans-4-[5-(p-alkyl- or p-n-alkoxyphenyl)-2-pyrimidinyl]cyclohexane carbonitrile of the formula

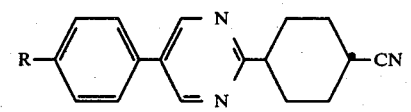

wherein R is straight-chain alkyl of 2 to 8 carbon atoms, straight-chain alkoxy of up to 6 carbon atoms or a branched-chain alkyl of the formula $C_2H_5—CH(CH_3)—(CH_2)_n$—wherein n is 1, 2 or 3.

4. In accordance with claim 1, a trans-4-[5-(trans-4-alkyl- or trans-4-n-alkoxycyclohexyl)-2-pyrimidinyl]cyclohexane carbonitrile of the formula

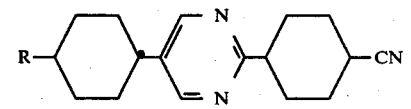

wherein R is straight-chain alkyl of 2 to 8 carbon atoms, straight-chain alkoxy of up to 6 carbon atoms or a branched-chain alkyl of the formula $C_2H_5—(CH(CH_3))—(CH_2)_n$—wherein n is 1, 2 or 3.

5. In accordance with claim 2, trans-p-[5-(4-ethylcyclohexyl)-2-pyrimidinyl]benzonitrile.

6. In accordance with claim 2, trans-p-[5-(4-pentylcyclohexyl)-2-pyrimidinyl]benzonitrile.

7. In accordance with claim 2, trans-p-[5-(4-heptylcyclohexyl)-2-pyrimidinyl]benzonitrile.

* * * * *